US009234078B2

(12) United States Patent
Sun et al.

(10) Patent No.: US 9,234,078 B2
(45) Date of Patent: Jan. 12, 2016

(54) CONJUGATED GOLD NANOPARTICLES

(71) Applicants: The Regents of the University of Michigan, Ann Arbor, MI (US); IMRA of America, Inc., Ann Arbor, MI (US)

(72) Inventors: Duxin Sun, Ann Arbor, MI (US); Hongwei Chen, Ann Arbor, MI (US); Wei Qian, Ann Arbor, MI (US); Yong Che, Ann Arbor, MI (US); Masayuki Ito, Cupertino, CA (US); Hayley Paholak, Ann Arbor, MI (US); Kanokwan Sansanaphongpricha, Ann Arbor, MI (US)

(73) Assignees: The Regents of the University of Michigan, Ann Arbor, MI (US); IMRA of America, Inc., Ann Arbor, MI (US)

( * ) Notice: Subject to any disclaimer, the term of this patent is extended or adjusted under 35 U.S.C. 154(b) by 0 days.

(21) Appl. No.: 14/212,594

(22) Filed: Mar. 14, 2014

(65) Prior Publication Data

US 2014/0296551 A1    Oct. 2, 2014

Related U.S. Application Data

(60) Provisional application No. 61/804,052, filed on Mar. 21, 2013.

(51) Int. Cl.
| | | |
|---|---|---|
| C08G 65/48 | (2006.01) | |
| A61K 47/48 | (2006.01) | |
| C08G 65/334 | (2006.01) | |
| A61K 41/00 | (2006.01) | |
| A61K 49/00 | (2006.01) | |

(52) U.S. Cl.
CPC ............ C08G 65/48 (2013.01); A61K 41/0052 (2013.01); A61K 47/48 (2013.01); A61K 47/48215 (2013.01); C08G 65/3344 (2013.01); *A61K 49/0065* (2013.01)

(58) Field of Classification Search
CPC ............... C08G 65/48; C08G 65/3344; A61K 41/0052; A61K 47/48215; A61K 47/48; A61K 49/0065
See application file for complete search history.

(56) References Cited

U.S. PATENT DOCUMENTS

| | | | |
|---|---|---|---|
| 8,679,859 | B2 | 3/2014 | Yan et al. |
| 8,697,129 | B2 | 4/2014 | Qian et al. |
| 2009/0169807 | A1 | 7/2009 | Yang et al. |
| 2011/0165647 | A1 | 7/2011 | Fernig et al. |
| 2011/0189695 | A1 | 8/2011 | Barcikowski et al. |
| 2012/0225021 | A1* | 9/2012 | Qian et al. .................. 424/9.6 |
| 2013/0052130 | A1* | 2/2013 | Davis et al. ................ 424/1.49 |

FOREIGN PATENT DOCUMENTS

| | | |
|---|---|---|
| WO | WO2005029076 | 3/2005 |
| WO | WO2006050257 | 5/2006 |
| WO | WO2007013877 | 2/2007 |
| WO | WO2014152941 | 9/2014 |

OTHER PUBLICATIONS

Amendola et al., Controlled size manipulation of free gold nanoparticles by laser irradiation and their facile bioconjugation, J. Mater. Chem., 2007, 17,4705-4710.
Arvizo et al., "Effect of nanoparticle surface charge at the plasma membrane and beyond", Nano Letters 2010, 10, 2543-2548.
Atkinson et al., "Thermal Enhancement with Optically Activated Gold Nanoshells Sensitizes Breast Cancer Stem Cells to Radiation Therapy", Sci Transl Med Oct. 27, 2010: vol. 2, Issue 55, p. 55ra79 DOI: 10.1126/scitranslmed.3001447.
Chen et al., "Enhanced Stability and Bioconjugation of Photo-Cross-Linked Polystyrene-Shell, Au-Core Nanoparticles", pp. 7491-7497, Langmuir 2007, 23, 7491.
Chen et al., "Gold Nanocages: Bioconjugation and Their Potential Use as Optical Imaging Contrast Agents", Nano Lett. 2005, 5, 473-477.
Csaki et al., "A Parallel Approach for Subwavelength Molecular Surgery Using Gene-Specific Positioned Metal Nanoparticles as Laser Light Antennas", Nano Lett. 2007, 7, 247-253.
Duchesne et al., "Robust ligand shells for biological applications of Gold nanoparticles", Langmuir 2008, vol. 24, 13572-13580.
El-Sayed et al., "Surface Plasmon Resonance Scattering and Absorption of anti-EGFR Antibody Conjugated Gold Nanoparticles in Cancer Diagnostics: Applications in Oral Cancer", Nano Lett. 2005, 5, 829-834.
Gobin et al., "Near-Infrared Resonant Nanoshells for Combined Optical Imaging and Photothermal Cancer Therapy", Nano Lett. 2007, 7, 1929-1934.
Haes, "Solution-Phase, Triangular Ag Nanotriangles Fabricated by Nanosphere Lithography", Journal of Physical Chemistry B, vol. 109 (2005), 11158.
Huang et al., "A Reexamination of Active and Passive Tumor Targeting by Using Rod-Shaped Gold Nanocrystals and Covalently Conjugated Peptide Ligands", ACS Nano Oct. 26, 2010, pp. 5887-5896 DOI: 10/1021/nn102055s.
Lee et al., Preparation and characterization of biodegradable nanoparticles entrapping immunodominant peptide conjugated with PEG for oral tolerance induction, J. of Controlled Release 105, p. 77-88 2005.
Liu et al., "Minimizing nonspecific phagocytic uptake of biocompatible gold nanoparticles with mixed charged zwitterionic surface modification", Journal of Materials Chemistry 2012, 22, 1916-1927.
Liu et al., "Synthesis, stability, and cellular internalization of Gold nanoparticles Containing Mixed Peptide-Poly(ethylene glycol) Monolayers", Anal. Chem 2007, 79, 2221-2229.

(Continued)

*Primary Examiner* — Sudhakar Katakam

(57) ABSTRACT

The present invention relates to methods, compositions, and kits for generating conjugated gold nanoparticles. In certain embodiments, the present invention provides methods of generating unsaturated conjugated gold nanoparticles by mixing naked gold nanoparticles with a first type of attachment molecules at a molar ratio such that the attachment molecules attach to the naked gold particles at a density level below the saturation level of the naked gold particles (e.g., at a saturation level of 1-99%). In some embodiments, a second type of attachment molecules (e.g., with the opposite charge as the first type of attachment molecules) are mixed with the unsaturated conjugated gold nanoparticles to generate double-conjugated gold nanoparticles (e.g., that are zwitterionic).

13 Claims, 11 Drawing Sheets

(56) References Cited

OTHER PUBLICATIONS

Na et al., "PEGylation of Octreotide: n. Effect of N-terminal Mono-PEGylation on Biological Activity and Pharmacokinetics", Pharmaceutical Research vol. 22, No. 5, May 2005 DOI: 10.1007/s11095-005-2590-y.

Nupponen et al., "Gold nanoparticles protected with ph and temperature-sensitive diblock copolymers", Langmuir 2007, 23:5352-5357.

Qian, "In vivo tumor targeting and spectroscopic detection with surface-enhanced Raman nanoparticle tags", Nat. Biotechnol. 2008, 26, 83 doi:10.1038/nbt1377.

Shan et al., "Recent advances in polymer protected gold nanoparticles: synthesis, properties and applications", Chem. Commun., 2007, 4580-4598 DOI: 10.1039/B707740H.

Simakin et al., "Nanodisks of Au and Ag produced by laser ablation in liquid environment", Chemical Physical letters 348 (2001) 182-186.

Tabor et al., "Dependence of the Threshold Energy of Femtosecond Laser Ejection of Gold Nanoprisms from Quartz Substrates on the Nanoparticle Environment", Journal of Physical Chemistry C, vol. 111 (2007), 8934-8941.

Vitale et al., "Mono- and bi-functional arenethiols as surfactants for gold nanoparticles: synthesis and characterization", Nanoscale Res Lett. Jan. 27, 2011;6(1):103. doi: 10.1186/1566-276X-6-103.

Wilson "The use of gold nanoparticles in diagnostics and detection", Chem. Soc. Rev., 2008, 37, 2028-2045 DOI: 10.1039/B712179M.

Yang et al., "Corrigendum: Development of Polymer-Encapsulated Metal Nanoparticles as Surface-Enhanced Raman Scattering Probes", Small 2011, 7, 2412 DOI: 10.1002/smll.201190063.

Yu et al., "Forming Biocompatible and Nonaggregated Nanocrystals in Water Using Amphiphilic Polymers", J. Am. Chem. Soc. 2007, 129, pp. 2871-2879.

Yuan et al., "Facile Synthesis of Highly Biocompatible Poly(2-(methacryloyloxy)ethyl phosphorylcholine)-Coated Gold Nanoparticles in Aqueous Solution", Langmuir 2006, 22, 11022-11027.

International Search Report and Written Opinion for PCT/US2014/028333, mailed Jul. 29, 2014, 15 pages.

* cited by examiner

CONJUGATED GOLD NANOPARTICLES

The present application claims priority to U.S. Provisional application Ser. No. 61/804,052, filed Mar. 21, 2013, which is herein incorporated by reference in its entirety.

STATEMENT REGARDING FEDERALLY SPONSORED RESEARCH OR DEVELOPMENT

This invention was made with government support under CA120023 awarded by the National Institutes of Health. The Government has certain rights in the invention.

TECHNICAL FIELD

The present invention relates to methods, compositions, and kits for generating conjugated gold nanoparticles. In certain embodiments, the present invention provides methods of generating unsaturated conjugated gold nanoparticles by mixing naked gold nanoparticles with a first type of attachment molecules at a molar ratio such that the attachment molecules attach to the naked gold particles at a density level below the saturation level of the naked gold particles (e.g., at a saturation level of 1-99%). In some embodiments, a second type of attachment molecules (e.g., with the opposite charge as the first type of attachment molecules) are mixed with the unsaturated conjugated gold nanoparticles to generate double-conjugated gold nanoparticles (e.g., that are zwitterionic).

BACKGROUND

Colloidal gold is a dispersion of gold nanoparticles in a colloidal suspension liquid, typically water but other liquids can also be used as discussed below. Gold nanoparticles (Au NPs) have attracted substantial interest from scientists for over a century because of their unique physical, chemical, and surface properties, such as: (i) size- and shape-dependent strong optical extinction and scattering which is tunable from ultraviolate (UV) wavelengths all the way to near infrared (NIR) wavelengths; (ii) large surface areas for conjugation to functional ligands; and (iii) little or no long-term toxicity or other adverse effects in vivo allowing their high acceptance level in living systems. Gold nanoparticles are now being widely investigated for their potential use in a wide variety of biological and medical applications as imaging contrast agents (*Nat. Biotechnol.* 2008, 26, 83 and *Nano Lett.* 2005, 5, 829), therapeutic agents (*Nano Lett.* 2007, 7, 1929 and *Sci. Transl. Med.* 2010, 2), biological sensors (*Chem. Soc. Rev.* 2008, 37, 2028), and cell-targeting vectors (*Nano Lett.* 2007, 7, 247).

Currently, the overwhelming majority of gold nanoparticles are prepared by using the standard wet chemical sodium citrate reduction of tetrachloroaurate ($HAuCl_4$) methodology. This method results in the synthesis of spherical gold nanoparticles with diameters ranging from 5 to 200 nanometers (nm) which are capped or covered with negatively charged citrate ions, which prevents the nanoparticles from aggregating by providing electrostatic repulsion.

Other wet chemical methods for formation of gold nanoparticles include the Brust method, the Perrault method and the Martin method. The Brust method relies on reaction of chlorauric acid with tetraoctylammonium bromide in toluene and sodium borohydride. The Perrault method uses hydroquinone to reduce the $HAuCl_4$ in a solution containing gold nanoparticle seeds. The Martin method uses reduction of $HAuCl_4$ in water by $NaBH_4$ wherein the stabilizing agents HCl and NaOH are present in a precise ratio. All of the wet chemical methods rely on first converting gold (Au) with strong acid into the atomic formula $HAuCl_4$ and then using this atomic form to build up the nanoparticles in a bottom-up type of process. All of the methods require the presence of stabilizing agents to prevent the gold nanoparticles from aggregating and precipitating out of solution.

On the other hand, over the past few decades, a physical method of making gold nanoparticles based on pulsed laser ablation of a gold target immersed in a liquid has been attracting increasingly widespread interest. In contrast to the chemical procedures, pulsed laser ablation of a gold target immersed in a liquid offers the possibility of generating stable gold nanocolloids while avoiding chemical precursors, reducing agents, and stabilizing ligands, all of which could be problematic for the subsequent functionalization and stabilization of the nanoparticles. Therefore, since it was pioneered by Henglein and Fojtik for preparing nano-size particles in either organic solvents or aqueous solutions as well as by Cotton for preparation of water-borne surface-enhanced Raman scattering active metallic nanoparticles with bare surfaces in 1993, the application of pulsed laser ablation of metal targets in liquids has gained much interest and has evolved as one of the most important physical method for obtaining colloidal gold nanoparticles, especially after the advent of femtosecond lasers, which are capable of eliminating some problems associated with the use of nanosecond lasers. Compared to laser ablation with pulses of longer duration, e.g. nanoseconds, the irradiation of metal targets by femtosecond laser pulses offers a precise laser-induced breakdown threshold and can effectively minimize the heat affected zones since the femtosecond laser pulses release energy to electrons in the target on a time-scale much faster than electron-phonon thermalization processes.

For most practical biomedical applications of gold nanoparticles, chemical stability in biological medium, biocompatibility, and targeting efficacy are the key requirements. Surface modifications are essential for meeting these requirements since interactions of gold nanoparticles with complex biological environments and biomolecules both on the surface of and inside the cells highly depend on the chemical nature of their solvent-accessible surface.

PEGylation, coating surface of gold nanoparticles with poly(ethylene glycol) (PEG) molecules, is the most commonly used surface modification approach to optimize the surface properties and functionalities of gold nanoparticles. For instance, a layer of PEG on the surface of gold nanoparticles enhances their solubility and stability under physiological conditions by providing a steric barrier. Also, when heterobifunctional PEG derivatives having amine (—$NH_2$) or carboxyl (—COOH) groups are incorporated onto surface of gold nanoparticles, these functional groups enable additional covalent surface modification with targeting ligands via conventional carbodiimide coupling chemistry (*Nat. Biotechnol.* 2008, 26, 83, *J. Phys. Chem. C* 2008, 112, 8127, *J. Am. Chem. Soc.* 2007, 129, 2871, and *ACS Nano* 2010, 4, 5887), which provides a route to further functionalization to generate targeting nanoparticles (*Langmuir* 2007, 23, 5352, *Langmuir* 2006, 22, 11022, *Nano Lett.* 2005, 5, 473, *Chem. Commun.* 2007, 4580, *Langmuir* 2007, 23, 7491, *Small* 2011, 7, 2412, and *Nanoscale Res. Lett.* 2011, 6).

Traditionally, surface modification of gold nanoparticles with PEG containing reactive functional groups, such as —COOH and —$NH_2$, requires a large excess amount of PEG, sometimes over a 10 fold excess, to prevent aggregation of the gold nanoparticles. It is undesirable to have the excess unreacted free PEG molecules left in the gold nanocolloids since it might interfere with or alter the expected functionalities of the gold nanoparticle conjugates formed. It is not easy, however, to remove the excess free ligand without inducing aggregation or leading to a noticeable loss of gold nanoparticle conjugates. Furthermore, because the PEG molecules must be added in such a large excess, it is not possible to prepare gold nanoparticles either with a defined number of PEG molecules per nanoparticle, which would be very beneficial for many applications and fundamental studies, or with multiple different types of PEG molecules with predetermined ratio. Finally, current surface modification of gold nanoparticles with PEG containing functional groups, such as —COOH and —NH$_2$, by adding to solution of gold nanoparticles a large excess of PEG molecules often results in highly charged surfaces, which promote strong non-specific binding to various cells and tissues. Consequently, after systemic administration these gold nanoparticles are rapidly cleared from the blood stream by the reticuloendothelial system (RES) and the mononuclear phagocytic system (MPS) in the liver, spleen, and bone marrow, resulting in reduced bioavailability of the targeting agents, a low therapeutic index and potential toxicity to healthy organs. Therefore, a technique granting the ability to control density of functional PEG molecules on surface of gold nanoparticles would have profound implications in biomedicine, for instance minimizing their macrophage recognition via optimizing surface charge (or zeta potential) of gold nanoparticle by controlling the ratio between the number of negative charged PEG molecules (such as PEG molecule terminated with COOH group at its distal end) and the number of positive charged PEG molecules (such as PEG molecule terminated with NH$_2$ group at its distal end) bound on their surface.

SUMMARY OF THE INVENTION

The present invention relates to methods, compositions, and kits for generating conjugated gold nanoparticles. In certain embodiments, the present invention provides methods of generating unsaturated conjugated gold nanoparticles by mixing naked gold nanoparticles with a first type of attachment molecules at a molar ratio such that the attachment molecules attach to the naked gold particles at a density level below the saturation level of the naked gold particles (e.g., at a saturation level of 1-99%). In some embodiments, a second type of attachment molecules (e.g., with the opposite charge as the first type of attachment molecules) are mixed with the unsaturated conjugated gold nanoparticles to generate double-conjugated gold nanoparticles (e.g., that are zwitterionic). In certain embodiments, the produced conjugated gold nanoparticles (e.g., with a zwitterionic surface) have a size in at least one dimension of from 1 to 200 nanometers and are stable in phosphate buffered saline (PBS) buffer for use in biological, medical, and other applications.

In some embodiments, the present invention provides methods for making conjugated gold nanoparticles comprising: a) providing: i) naked gold nanoparticles, wherein each of the naked gold nanoparticles has an gold surface, and wherein at least 90% (e.g., at least 90% . . . 93% . . . 95%) of the gold surface is exposed and not attached to any molecules, and ii) first type of attachment molecules having the formula R1-polymer-R2, wherein R1 is a moiety having affinity for the gold surface of the naked gold nanoparticles, and wherein R2 is a functional group that allows attachment to other chemicals, and/or comprises a targeting ligand; and b) mixing the first type of attachment molecules with the naked gold nanoparticles in a first molar ratio of the first type of attachment molecules to the naked gold nanoparticles such that the first type of attachment molecules attach to the naked gold nanoparticles at a density level below the saturation level for the naked gold nanoparticles thereby generating unsaturated conjugated gold nanoparticles.

In certain embodiments, the molar ratio of the first type of attachment molecules to the naked gold particles is such that the density level is about 1-99% of the saturation level (e.g., 1% . . . 10% . . . 25.5% . . . 50% . . . 75% . . . 90% . . . 98% . . . 99.5%).

In other embodiments, the methods further comprise providing a second type of attachment molecules having the formula R3-polymer-R4, wherein R3 is a moiety having affinity for the gold surface of the unsaturated conjugated gold nanoparticles, and wherein R4 is a functional group that allows attachment to other chemicals, and/or comprises a targeting ligand, and wherein the method further comprises c) mixing the second type of attachment molecules with the unsaturated conjugated gold nanoparticles in a second molar ratio of the second type of attachment molecules to the unsaturated conjugated gold particles such that the second type of attachment molecules attach to the unsaturated conjugated gold nanoparticles thereby generated double-conjugated gold nanoparticles. In some embodiments, the first type of attachment molecules posses a positive charge and the second type of attachment molecules possess a negative charge, such that the double-conjugated gold nanoparticles are zwitterionic. In further embodiments, the first type of attachment molecules posses a negative charge and the second type of attachment molecules possess a positive charge, such that the double-conjugated gold nanoparticles are zwitterionic.

In some embodiments, the methods further comprise providing a third type of attachment molecules having the formula R5-polymer-R6, wherein R5 is a moiety having affinity for the gold surface of the double-conjugated gold nanoparticles, and wherein R6 is a functional group that allows attachment to other chemicals, and/or comprises a targeting ligand, and wherein the method further comprises d) mixing the third type of attachment molecules with the double-conjugated gold nanoparticles in a third molar ratio of the third type of attachment molecules to the double-conjugated gold particles such that the third type of attachment molecules attach to the double-conjugated gold nanoparticles thereby generated third-conjugated gold nanoparticles.

In particular embodiments, the first molar ratio is from 1 to 700 (e.g., 1 . . . 100 . . . 200 . . . 350 . . . 500 . . . 700). In other embodiments, the second molar ratio is from 1 to 500 (e.g., 1 . . . 150 . . . 300 . . . 500). In certain embodiments, R1 is the same or different on each of the first type of attachment molecules and is selected from the group consisting of: a thiol group, an amine group, a phosphine group, and a disulfide group. In further embodiments, R3 is the same or different on each of the second type of attachment molecules and is selected from the group consisting of: a thiol group, an amine group, a phosphine group, and a disulfide group.

In some embodiments, the polymer is the first type of attachment molecules comprises polyethylene glycol. In other embodiments, the polymer in the first type of attachment molecules is selected from the group consisting of: polyethyleneglycol (PEG), polyacrylamide, polydecylmethacrylate, polystyrene, dendrimer molecule, polycaprolactone (PCL), polylactic acid (PLA), poly(lactic-co-glycolic acid) (PLGA), polyglycolic acid (PGA), polyhydroxybutyrate (PHB), and the polymer has degree of polymerization in the range from 1 unit to 100 units.

In certain embodiments, the polymer in the second type of attachment molecules comprises polyethylene glycol. In other embodiments, the polymer in the second type of attachment molecules is selected from the group consisting of: polyethyleneglycol (PEG), polyacrylamide, polydecylmethacrylate, polystyrene, dendrimer molecule, polycaprolactone (PCL), polylactic acid (PLA), poly(lactic-co-glycolic acid) (PLGA), polyglycolic acid (PGA), polyhydroxybutyrate (PHB), and the polymer has degree of polymerization in the range from 1 unit to 100 units.

In particular embodiments, R2 is selected from the group consisting of COOH, —OCH$_3$, and —NH$_2$. In further embodiments, R4 is selected from the group consisting of COOH, —OCH$_3$, and —NH$_2$. In other embodiments, at least 93% of the gold surface of each of the naked gold nanoparticles is exposed and not attached to any molecules. In further embodiments, the naked gold nanoparticles are in a colloidal suspension. In some embodiments, the naked gold nanoparticles are pulse laser ablation generated naked gold nanoparticles.

In certain embodiments, the present invention provides compositions comprising: unsaturated conjugated gold nanoparticles, wherein the unsaturated conjugated gold nanoparticles comprise: a) gold nanoparticles, and b) a first type of attachment molecules attached to the gold nanoparticles at a density level below the saturation level for the gold nanoparticles, wherein the first type of attachment molecules have the formula R1-polymer-R2, wherein R1 is a moiety having affinity for the gold surface of the naked gold nanoparticles, and wherein R2 is a functional group that allows attachment to other chemicals, and/or comprises a targeting ligand. In some embodiments, the first type of attachment molecules are attached to the gold nanoparticles at a density level of about 1-99% of the saturation level.

In some embodiments, the present invention provides methods which permit versatile and controllable surface modification of gold nanoparticles with both positive charged PEG and negative charged PEG (e.g., for addressing the issues and challenges described above) and methods of fabricating gold nanoparticles with zwitterionic surface, which are gold nanoparticles containing both positive and negative charges on the same gold nanoparticle. It is believed that, prior to the present invention, there was no way to conjugate a defined number of positive charged ligands and negative charged ligands onto the surface of gold nanoparticles to control the surface charge (or zeta potential) for optimizing their biomedical performance. Colloidal gold nanoparticles used in work conducted during development of the present invention were fabricated by femtosecond laser ablation of gold targets in deionized water. The produced gold nanoparticles have a bare surface and are in a contamination-free environment.

In one aspect, the present invention is directed to conjugate both negative charged PEG molecules (e.g., PEG molecules terminated with COOH groups at their distal end) and positive charged PEG molecules (e.g., PEG molecules terminated with NH$_2$ group at their distal end) onto surface of the same gold nanoparticle in a sequential manner, which permits precisely control of number of both negative charged PEG molecules and positive charged PEG molecules bound onto the surface of a gold nanoparticle. In certain embodiments, both negative charged PEG molecules and positive charged PEG molecules contain at least one thiol which could form Au—S interaction with gold nanoparticle.

In another aspect, the present invention is directed to demonstrate that by controlling density of different functional PEG molecules with opposite charges bound onto surface of the same gold nanoparticle, the non-specific cellular uptake of such gold nanoparticles with zwitterionic surface by macrophage cells could be minimized.

In certain embodiments, the present invention provides methods of producing stable colloidal gold nanoparticles with zwitterionic surface comprising the steps of: a) preparing a stable colloidal suspension of naturally negative charged gold nanoparticles in a colloidal suspension liquid by the standard wet chemical sodium citrate reduction of tetrachloroaurate (HAuCl$_4$) methodology or a top-down nanofabrication method using bulk gold as a source material, preparing a solution of negative charged ligands in said colloidal suspension liquid, and preparing a solution of positive charged ligands in said colloidal suspension liquid, said negative charged ligand and positive charged ligand contain at least one functional group having an affinity for surface of said gold nanoparticles; b) performing surface modification of said gold nanoparticles for forming zwitterionic surface by conjugation of both said negative charged ligands and positive charged ligands onto surface of said colloidal gold nanoparticles in a sequential manner, said negative charged ligands were first mixed with said colloidal suspension of gold nanoparticles at room temperature for at least 30 minutes and then followed by addition of said positive charged ligands to said colloidal suspension of gold nanoparticles also at room temperature, the total amount of said negative charged ligand added to the said colloidal gold nanoparticles is no more than the minimum amount required to provide a monolayer of bound said negative charged ligand to the total of said colloidal gold nanoparticles based on a footprint of said negative charged ligand bound on said gold nanoparticles and total amount of said positive charged ligand added to the said colloidal gold nanoparticles is no more than the minimum amount required to bind to all free binding sites left on surface of said colloidal gold nanoparticles after conjugation of said negative charged ligands onto surface of said colloidal gold nanoparticles, after mixing, the said mixture was kept undisturbed for 24 hours at room temperature to provide a sufficient amount of time for both said positive charged ligands and negative charged ligands to be conjugated onto the surfaces of said colloidal Au nanoparticles; and c) optionally, adding to said colloidal gold nanoparticles more said negative charged ligands to ensure saturation of said binding sites on surface of said colloidal gold nanoparticles for maximizing colloidal stability of said colloidal gold nanoparticles.

In particular embodiments, the top-down nanofabrication methods in step a) comprise applying a physical energy source to a source of bulk gold in a colloidal suspension liquid, said physical energy source comprising at least one of mechanical energy, heat energy, electric field arc discharge energy, magnetic field energy, ion beam energy, electron beam energy, or laser beam energy. In certain embodiments, the top-down nanofabrication methods in step a) comprise a two-step process comprising first fabricating a gold nanoparticle array on a substrate by using photo, electron beam, focused ion beam, or nanosphere lithography and secondly removing said gold nanoparticle arrays from said substrate in a colloidal suspension liquid. In certain embodiments, the top-down nanofabrication methods comprise applying laser ablation to said source of bulk gold in a colloidal suspension liquid. In further embodiments, the naturally negative charged gold nanoparticles in a colloidal suspension liquid in step a) comprises a population of gold nanoparticles wherein said gold nanoparticles have at least one dimension in the range of from 1 to 200 nanometers (e.g., 1 . . . 37 . . . 55 . . . 84 . . . 128 . . . 165 . . . 191 . . . 200 nanometers). In some embodiments, the naturally negative charged gold nanoparticles in a colloidal suspension liquid in step a) comprises a population of gold nanoparticles wherein the shape of said gold nanoparticles comprises at least one of a sphere, a rod, a prism, a disk, a cube, a core-shell structure, a cage, a frame, or a mixture thereof.

In certain embodiments, the negative charged ligand in step a) comprises a polymer containing at least one functional group having an affinity for surface of said gold nanoparticles and at least one negative charged group at the end of side polymer distal to said functional group having an affinity for surface of gold nanoparticles. In other embodiments, the polymer comprises but not limited to polyethyleneglycol (PEG), polyacrylamide, polydecylmethacrylate, polystyrene, dendrimer molecule, polycaprolactone (PCL), polylactic acid (PLA), poly(lactic-co-glycolic acid) (PLGA), polyglycolic acid (PGA), polyhydroxybutyrate (PHB), and the said polymer having degree of polymerization in the range from 1 unit to 100 units. In further embodiments, the functional group having an affinity for surface of said gold nanoparticles in step a) comprises but not limited to thiol group, amine group, phosphine group, disulfide group or a mixture thereof. In certain embodiments, the polymer comprises polyethyleneglycol (PEG) containing thiol group and carboxyl group at the end of PEG distal to said thiol group. In some embodiments, the polyethyleneglycol (PEG) has a molecular weight in the range of from 200 Daltons to 100,000,000 Daltons.

In some embodiments, the positive charged ligand in step a) comprises a polymer containing at least one functional group having an affinity for surface of said gold nanoparticles and at least one positive charged group at the end of side polymer distal to said functional group having an affinity for surface of gold nanoparticles. In certain embodiments, the polymer comprises but not limited to polyethyleneglycol (PEG), polyacrylamide, polydecylmethacrylate, polystyrene, dendrimer molecule, polycaprolactone (PCL), polylactic acid (PLA), poly(lactic-co-glycolic acid) (PLGA), polyglycolic acid (PGA), polyhydroxybutyrate (PHB), and wherein, in some embodiments, the polymer has a degree of polymerization in the range from 1 unit to 100 units (e.g., 1 . . . 25 . . . 50 . . . 75 . . . 100). In certain embodiments, the polymer comprises polyethyleneglycol (PEG) containing thiol group and amine group at the end of PEG distal to said thiol group. In other embodiments, the polyethyleneglycol (PEG) having a molecular weight in the range of from 200 Daltons to 100,000,000 Daltons.

In some embodiments, the colloidal suspension liquid in step a) comprises but not limited to water, methanol, ethanol, acetone, and dimethylformamide. In other embodiments, the footprint of said negative charged ligand or positive charged ligand in step b) is determined by dynamic light scattering during said negative charged ligand or positive charged ligand conjugation to said colloidal gold nanoparticles, by reference to literature values, or by a mixture of these methods. In certain embodiments, the negative charged ligand added to the said colloidal gold nanoparticles in step b) comprises from 1 to 100% of the amount necessary to form a monolayer of said negative charged ligand on said gold nanoparticles. In other embodiments, the amount of said positive charged ligand added to the said colloidal gold nanoparticles in step b) comprises from 1 to 100% of the amount necessary to form a monolayer of said positive charged ligand on said gold nanoparticles. In further embodiments, the methods further comprises d), after step b) or step c), removing said colloidal gold nanoparticles conjugated with both said negative charged ligands and positive charged ligands from said colloidal suspension and creating a powder of the same.

In some embodiments, the present invention provides stable colloidal gold nanoparticles with zwitterionic surface comprising: a population of naturally negative charged colloidal gold nanoparticles conjugated with both negative charged ligands and positive charged ligands in a colloidal suspension liquid, individual amounts of said negative charged ligand and said positive charged ligand bound to surface of said colloidal gold nanoparticles could be independently tuned to be any amount providing surface coverage of said negative charged ligand and said positive charged ligand on surface of said colloidal gold nanoparticles between 1 and 100% based on footprints of said negative charged ligand and said positive charged ligand bound on said gold nanoparticles, and said negative charged ligand and positive charged ligand contain at least one functional group having an affinity for surface of said gold nanoparticles.

In certain embodiments, said colloidal gold nanoparticles with zwiterionic surface having zeta potential in said colloidal suspension liquid greater than −30 mV. In further embodiments, said colloidal gold nanoparticles with zwiterionic surface having zeta potential in said colloidal suspension liquid greater than −20 mV. In some embodiments, the naturally negative charged colloidal gold nanoparticles have been created by a top-down fabrication method comprising applying a physical energy source to a source of bulk gold in a colloidal suspension liquid, said physical energy source comprising at least one of mechanical energy, heat energy, electric field arc discharge energy, magnetic field energy, ion beam energy, electron beam energy, or laser beam energy. In further embodiments, the naturally negative charged colloidal gold nanoparticles have been created by a top-down fabrication method comprising applying laser ablation to said source of bulk gold in a colloidal suspension liquid.

In some embodiments, the naturally negative charged colloidal gold nanoparticles have been created by a top-down fabrication method further comprising the step of first fabricating said source of bulk gold as a gold nanoparticle array on a substrate by photo electron beam deposition, focused ion beam deposition, or nanosphere lithography deposition and then using said gold nanoparticle array on said substrate as said source of bulk gold in a colloidal suspension liquid. In other embodiments, the naturally negative charged colloidal gold nanoparticles have at least one dimension in the range of from 1 to 200 nanometers (e.g., 1 . . . 50 . . . 100 . . . 167 . . . 200 nanometers). In certain embodiments, the naturally negative charged colloidal gold nanoparticles in a colloidal suspension liquid comprises a population of gold nanoparticles wherein the shape of said gold nanoparticles comprises at least one of a sphere, a rod, a prism, a disk, a cube, a core-shell structure, a cage, a frame, or a mixture thereof. In other embodiments, the negative charged ligand comprise polymer containing at least one functional group having an affinity for surface of said gold nanoparticles and at least one negative charged group at the end of side polymer distal to said functional group having an affinity for surface of gold nanoparticles.

In certain embodiments, the polymer comprises, but is not limited to, polyethyleneglycol (PEG), polyacrylamide, polydecylmethacrylate, polystyrene, dendrimer molecule, polycaprolactone (PCL), polylactic acid (PLA), poly(lactic-co-glycolic acid) (PLGA), polyglycolic acid (PGA), polyhydroxybutyrate (PHB), and, in certain embodiments, the polymer has a degree of polymerization in the range from 1 unit to 100 units (e.g., 1 . . . 43 . . . 67 . . . 100 units). In certain embodiments, the functional group has an affinity for surface of said gold nanoparticles and is selected from, but not limited to, a thiol group, an amine group, an phosphine group, an disulfide group or a mixture thereof. In particular embodiments, the polymer comprises polyethyleneglycol (PEG) containing thiol group and carboxyl group at the end of PEG distal to said thiol group. In further embodiments, the polyethyleneglycol (PEG) has a molecular weight in the range of from 200 Daltons to 100,000,000 Daltons. In other embodiments, the positive charged ligand comprise polymer containing at least one functional group having an affinity for surface of said gold nanoparticles and at least one positive charged group at the end of side polymer distal to said functional group having an affinity for surface of gold nanoparticles. In certain embodiments, the polymer is selected from: polyethyleneglycol (PEG), polyacrylamide, polydecylmethacrylate, polystyrene, dendrimer molecule, polycaprolactone (PCL), polylactic acid (PLA), poly(lactic-co-glycolic acid) (PLGA), polyglycolic acid (PGA), polyhydroxybutyrate (PHB). In other embodiments, the polymer has degree of polymerization in the range from 1 unit to 100 units. In certain embodiments, the polymer comprises polyethyleneglycol (PEG) containing thiol group and amine group at the end of PEG distal to said thiol group. In other embodiments, the polyethyleneglycol (PEG) having a molecular weight in the range of from 200 Daltons to 100,000,000 Daltons. In additional embodiments, the colloidal suspension liquid comprises but not limited to water, methanol, ethanol, acetone, and dimethylformamide.

In some embodiments, the footprint of said negative charged ligand or positive charged ligand is determined by dynamic light scattering during said negative charged ligand or positive charged ligand conjugation to said colloidal gold nanoparticles, by reference to literature values, or by a mixture of these methods. In other embodiments, the gold nanoparticles with zwitterionic surface are a powder.

In certain embodiments, the present invention provides a stable colloidal solution of gold nanoparticles with zwitterionic surface fabricated by the methods described above and herein.

DETAILED DESCRIPTION

Figure 1:
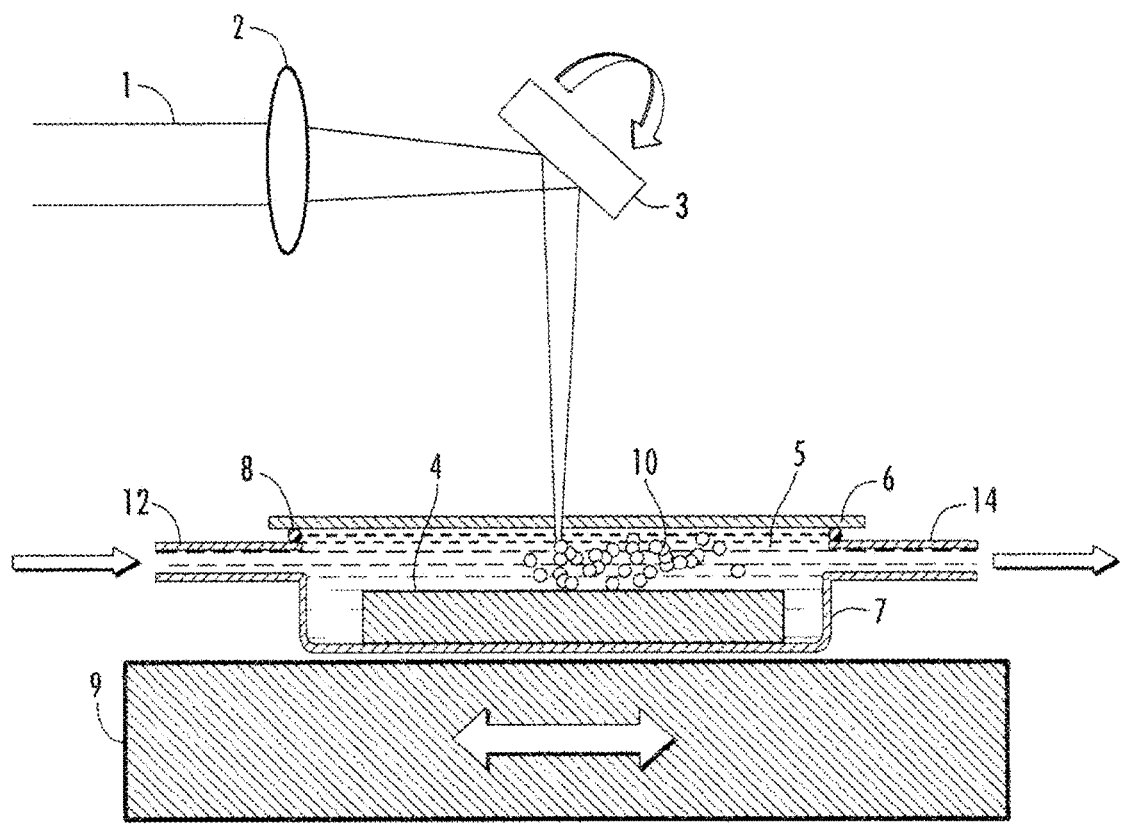
FIG. 1. Schematic illustration of a laser-based ablation system for the top-down production of gold nanoparticles in a organic solvent in accordance with the present invention.

Gold nanocolloids have attracted strong interest from scientists for over a century and are now being heavily investigated for their potential use in a wide variety of medical and biological applications. For example, potential uses include surface-enhanced spectroscopy, biological labeling and detection, gene-regulation, and diagnostic or therapeutic agents for treatment of cancer in humans. Their versatility in a broad range of applications stems from their unique physical, chemical, and surface properties, such as: (i) size- and shape-dependent strong optical extinction and scattering at visible and near infrared (NIR) wavelengths due to a localized surface plasmon resonance of their free electrons upon excitation by an electromagnetic field; (ii) large surface areas for conjugation to functional ligands; and (iii) little or no long-term toxicity or other adverse effects in vivo allowing their high acceptance level in living systems.

These new physical, chemical, and surface properties, which are not available from either atomic or bulk counterparts, explain why gold nanocolloids have not been simply chosen as alternatives to molecule-based systems but as novel structures which provide substantive advantages in biological and medical applications.

The prerequisite for most of intended biological and medical applications of gold nanoparticles is the further surface modification of the as-synthesized gold nanoparticles via conjugation of functional ligand molecules to the surface of the gold nanoparticles. The surface functionalization of gold nanoparticles for any biological or medical applications is crucial for at least two reasons. First is control over the interaction of the nanoparticles with their environment, which is naturally taking place at the nanoparticle surface. Appropriate surface functionalization is a key step to providing stability, solubility, and retention of physical and chemical properties of the nanoparticles in the physiological conditions. Second, the ligand molecules provide additional and new properties or functionality to those found inherently in the core gold nanoparticle. These conjugated gold nanoparticles bring together the unique properties and functionality of both the core material and the ligand shell for achieving the goals of highly specific targeting of gold nanoparticles to the sites of interest, ultra-sensitive sensing, and effective therapy.

Nowadays, the major strategy for surface modification of gold nanoparticles include coating gold nanoparticles with polymer, for example PEG containing reactive functional groups, such as —COOH and —NH$_2$, which are ready for the conjugation of targeting ligands. However, current strategy of coating gold nanoparticles with functional groups, such as —COOH and —NH$_2$, often results in highly charged surfaces, which promote their binding to biomolecules in the biological systems through ionic interactions, causing nanoparticles to aggregate in biological environments and thus exhibit strong non-specific binding to various cells and tissues that is undesirable in many in vitro and in vivo applications.

In the present invention, provided are methods which permits versatile and controllable surface modification of gold nanoparticles with both positive charged PEG and negative charged PEG (e.g., for addressing the issues and challenges described above) and provide methods to fabricate gold nanoparticles having minimum cellular uptake by macrophage cells via forming zwitterionic surface containing both positive and negative charges on the same gold nanoparticle. It is believed that, prior to the present invention, there was no way to conjugate a defined number of positive charged ligands and negative charged ligands onto the surface of gold nanoparticles to control the surface charge (or zeta potential) for optimizing their biomedical performance.

As discussed above, the overwhelming majority of gold nanoparticles are prepared by the standard sodium citrate reduction reaction. This method allows for the synthesis of spherical gold nanoparticles with diameters ranging from 5 to 200 nanometers (nm) which are capped with negatively charged citrate ions. The capping controls the growth of the nanoparticles in terms of rate, final size, geometric shape and stabilizes the nanoparticles against aggregation by electrostatic repulsion.

In contrast to the prior process of bottom-up fabrication using wet chemical processes, in certain embodiments, the gold nanoparticles used in the present invention are produced by a top-down nanofabrication approach. The top-down fabrication methods of the present invention start with a bulk material in a liquid and then break the bulk material into nanoparticles in the liquid by applying physical energy to the material. The physical energy can be mechanical energy, heat energy, electric field arc discharge energy, magnetic field energy, ion beam energy, electron beam energy, or laser beam energy including laser ablation of the bulk material. The present process produces a pure, bare colloidal gold nanoparticle that is stable in the ablation liquid. The ablation liquids comprise a plurality of solvents selected from but not limited to deionized water, methanol, ethanol, acetone, and dimethylformamide.

The present invention is noted limited by the top-down nanofabrication approach used in the present invention. These methods involve the generation of the nanoparticles from the bulk material in the presence of the suspension medium. In one embodiment the process comprises a one step process wherein the application of the physical energy source, such as mechanical energy, heat energy, electric field arc discharge energy, magnetic field energy, ion beam energy, electron beam energy, or laser energy to the bulk gold occur in the suspension medium. The bulk source is placed in the suspension medium and the physical energy is applied thus generating nanoparticles that are immediately suspended in the suspension medium as they are formed. In another embodiment the present invention employs a two-step process including the steps of: 1) fabricating gold nanoparticle arrays on a substrate by using photo, electron beam, focused ion beam, nanoimprint, or nanosphere lithography as known in the art; and 2) removing the gold nanoparticle arrays from the substrate into the suspension liquid using one of the physical energy methods. Tabor, C., Qian, W., and El-Sayed, M. A., Journal of Physical Chemistry C, Vol 111 (2007), 8934-8941; Haes, A. J.; Zhao, J.; Zou, S. L.; Own, C. S.; Marks, L. D.; Schatz, G. C.; Van Duyne, R. P. Journal Of Physical Chemistry B, Vol 109 (2005), 11158. In both methods the colloidal gold is formed in situ by generating the nanoparticles in the suspension medium using one of the physical energy methods.

In certain embodiments of the present invention, colloidal suspensions of gold nanoparticles are produced by pulsed laser ablation of a bulk gold target in deionized water as the suspension medium. FIG. 1 schematically illustrates a laser-based system for producing colloidal suspensions of nanoparticles of complex compounds such as gold in a organic liquid using pulsed laser ablation. In certain embodiments, a laser beam 1 is generated from an ultrafast pulsed laser source, not shown, and focused by a lens 2. The source of the laser beam 1 can be a pulsed laser or any other laser source providing suitable pulse duration, repetition rate, and/or power level as discussed below. The focused laser beam 1 then passes from the lens 2 to a guide mechanism 3 for directing the laser beam 1. Alternatively, the lens 2 can be placed between the guide mechanism 3 and a target 4 of the bulk material. The guide mechanism 3 can be any of those known in the art including piezo-mirrors, acousto-optic deflectors, rotating polygons, a vibration mirror, or prisms. Preferably the guide mechanism 3 is a vibration mirror 3 to enable controlled and rapid movement of the laser beam 1. The guide mechanism 3 directs the laser beam 1 to a target 4. In one embodiment, the target 4 is a bulk gold target. The target 4 is submerged a distance, from several millimeters to preferably less than 1 centimeter, below the surface of a suspension organic liquid 5. The target 4 is positioned in a container 7 additionally but not necessarily having a removable glass window 6 on its top. Optionally, an O-ring type seal 8 is placed between the glass window 6 and the top of the container 7 to prevent the liquid 5 from leaking out of the container 7. Additionally but not necessarily, the container 7 includes an inlet 12 and an outlet 14 so the liquid 5 can be passed over the target 4 and thus be re-circulated. The container 7 is optionally placed on a motion stage 9 that can produce translational motion of the container 7 with the target 4 and the liquid 5. Flow of the liquid 5 is used to carry the nanoparticles 10 generated from the target 4 out of the container 7 to be collected as a colloidal suspension. The flow of liquid 5 over the target 4 also cools the laser focal volume. The liquid 5 can be any liquid that is largely transparent to the wavelength of the laser beam 1, and that serves as a colloidal suspension medium for the target material 4. In one embodiment, the liquid 5 is deionized water. The system thus allows for generation of colloidal gold nanoparticles in situ in a suspension liquid so that a colloidal gold suspension is formed. The formed gold nanoparticles are immediately stably suspended in the liquid and thus no dispersants, stabilizer agents, surfactants or other materials are required to maintain the colloidal suspension in a stable state.

In work conducted during the development of embodiments of the present invention, the following laser parameters were used to fabricate gold nanocolloids by pulsed laser ablation of a bulk gold target in acetone: pulse energy of 10 uJ (micro Joules), pulse repetition rate of 100 kHz, pulse duration of 700 femtoseconds, and a laser spot size on the ablation target of about 50 um (microns). For the preparation of Au nanocolloids a 16 mm (millimeter) long, 8 mm wide, and 0.5 mm thick rectangular target of Au from Alfa Aesar was used. For convenience, the Au target materials can be attached to a bigger piece of a bulk material such as a glass slide, another metal substrate, or a Si substrate.

More generally, for the present invention the laser ablation parameters are as follows: a pulse duration in a range from about 10 femtoseconds to about 500 picoseconds, preferably from about 100 femtoseconds to about 30 picoseconds; the pulse energy in the range from about 1 µJ to about 100 µJ; the pulse repetition rate in the range from about 10 kHz to about 10 MHz; and the laser spot size may be less than about 100 µm. The target material has a size in at least one dimension that is greater than a spot size of a laser spot at a surface of the target material.

Figure 2:
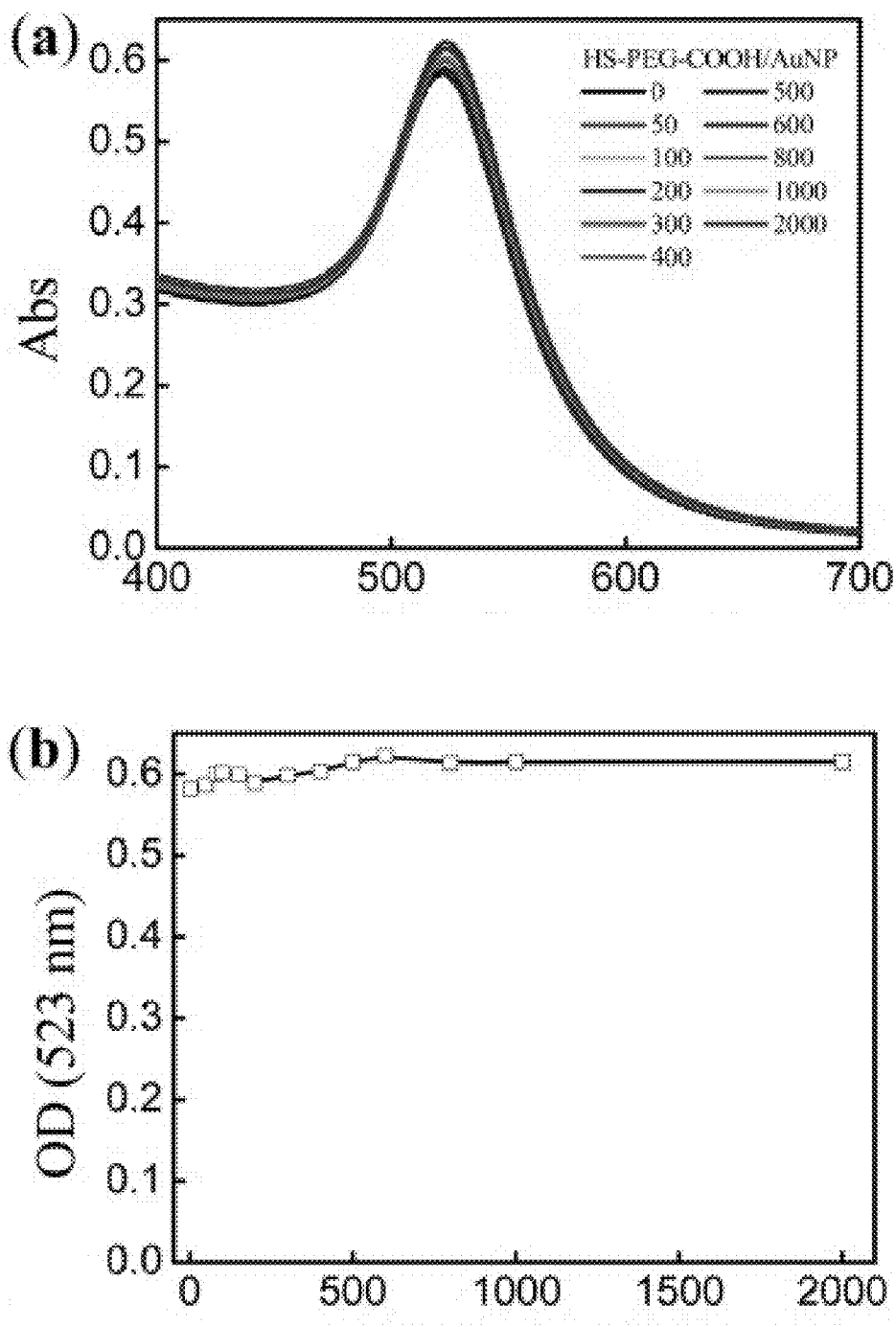
FIGS. 2a-d. (a) Absorption spectra at typical molar ratios, (b) optical density at absorption peak, (c) zeta potential, and (d) hydrodynamic size change of gold nanoparticles PEGylated with HS-PEG-COOH at each molar ratio before centrifugation, where the insert shows a schematic illustration of the conformational change of PEGylated chains on gold nanoparticles from mushroom at lower PEG chain densities to brush at higher PEG chain densities.
Figure 2:
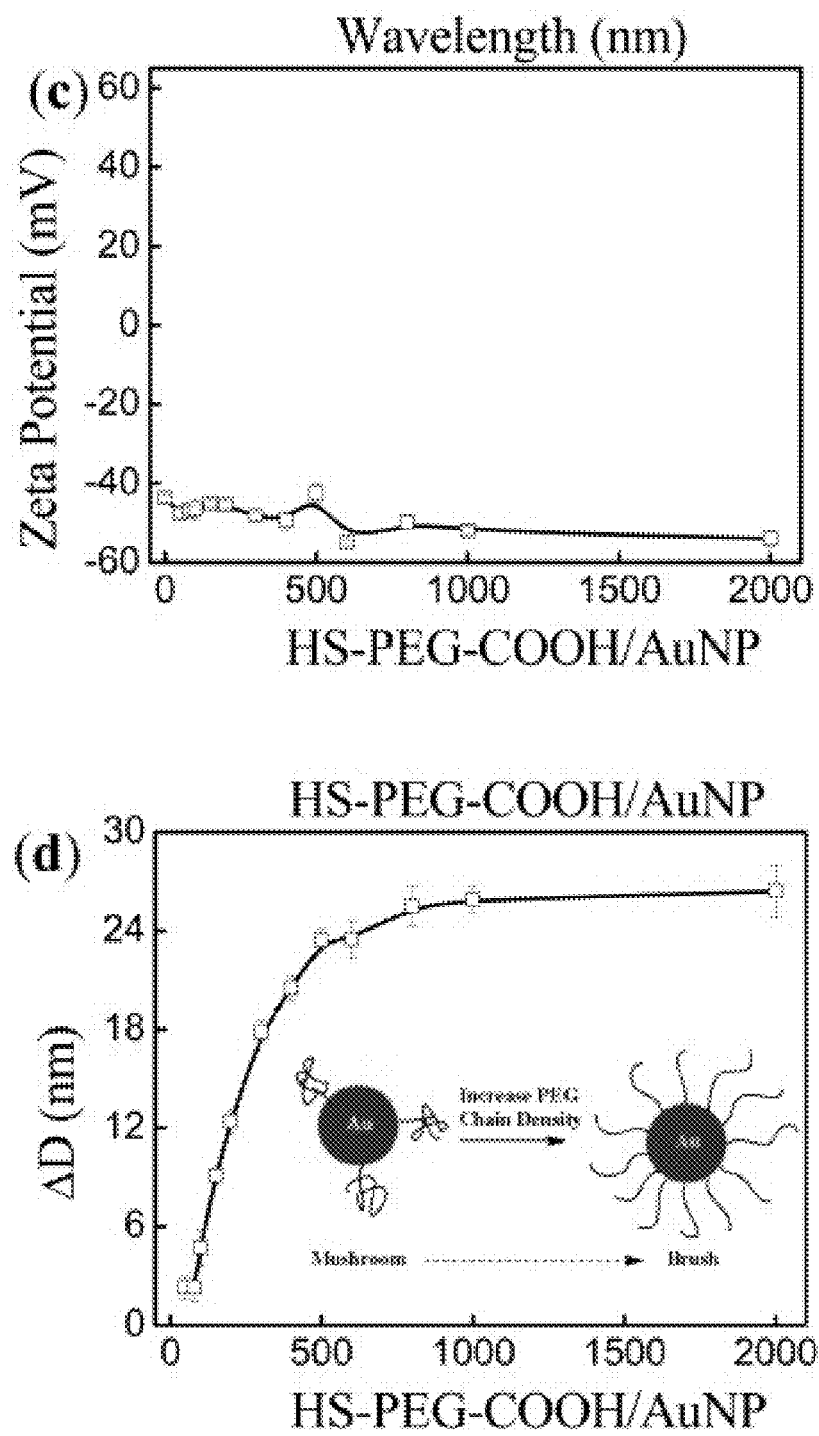

Work conducted during the development of embodiments of the present invention found that stable colloidal solution of gold nanoparticles with only partial surface modification could be fabricated. Also, the surface coverage amount of functional PEG molecules on the surface of the gold nanoparticles can be tuned to be any percent value between 0 and 100%. FIG. 2 shows the physical characteristics of AuNPs (~20 nm in diameter based on TEM imaging) after mixing with HS-PEG-COOH (thiolated negative charged PEG molecule terminated with carboxyl group at its distal end) with different HS-PEG-COOH/AuNP molar ratios from zero to 2000. This molar ratio range was chosen based on the surface area of 20-nm AuNPs and the footprint of PEG molecules. For PEGylation we selected thiolated $PEG_{5000}$ with molecular weight of 5000 Daltons, which is most widely used to modify gold nanoparticles. The thiol concentration (>95%) was confirmed by an Ellman's test. During PEGylation, the Au nanoparticle concentration was fixed at 1.0 nM, determined by correlating our measured extinction spectra to the experimentally determined extinction cross-section data ($8.8\times10^8$ $M^{-1}cm^{-1}$ for AuNPs with a diameter of 20 nm). FIGS. 2a and 2b show the optical spectra of AuNPs at all HS-PEG-COOH/AuNP ratios and the corresponding optical density (OD) at the absorption peak, respectively. The overlapping curves and the constant OD reveal that there is no loss of AuNPs after PEGylation for each of the HS-PEG-COOH/AuNP molar ratio.

The high colloidal stability of laser-made AuNPs after PEGylation with different molar ratios is probably attributed to the highly negatively charged surface as displayed in FIG. 2c, which shows that the zeta potential is independent of the HS-PEG-COOH/AuNP molar ratio. Although there are not any capping ligands on the AuNP surfaces before PEGylation, the AuNPs made by femtosecond pulse laser ablation have a natural negative surface with zeta potential of about −33.3 mV. The negatively charged surface is caused by partial oxidation from the oxygen present in solution, followed by proton transfer to adjacent hydroxide ions.

The PEGylation process was further demonstrated by monitoring the change in particle size after PEGylation with increasing HS-PEG-COOH/AuNP molar ratios, as shown in FIG. 2d. The data show that the hydrodynamic layer thickness consistently increased with increasing molar ratios of HS-PEG-COOH/AuNP, and reached a constant at 26 nm after the AuNP surface was saturated at molar ratio of 500. This reveals an increase in PEG chain density on AuNP surfaces upon increasing the HS-PEG-COOH/AuNP molar ratio. For free PEG molecules in a good solvent, the radius of gyration $R_g$ can be empirically calculated by:

$$R_g[nm] = 0.181 \times N^{0.58}$$

where N is the number of ethylene glycol (EG) monomer units per PEG chain. For the $PEG_{5000}$ used here, $R_g$ is 2.8 nm and the size increase should be around 11.2 nm (2.8×4) if the PEG chains form isolated hemispheres (mushroom) on the surface with a critical PEG density $\sigma^*(1/\pi R_g^2)$ around 0.04 $PEG/nm^2$. At molar ratio of 500 the PEG density σ is around 0.4 $PEG/nm^2$, which is 10 times higher than the critical grafting density. The grafting PEG chains are most likely reconfigured, stretching out in a brush conformation as shown in the insert of FIG. 1d. This explains why the hydrodynamic layer thickness (ΔD) is more than four times the radius of gyration.

Figure 3:
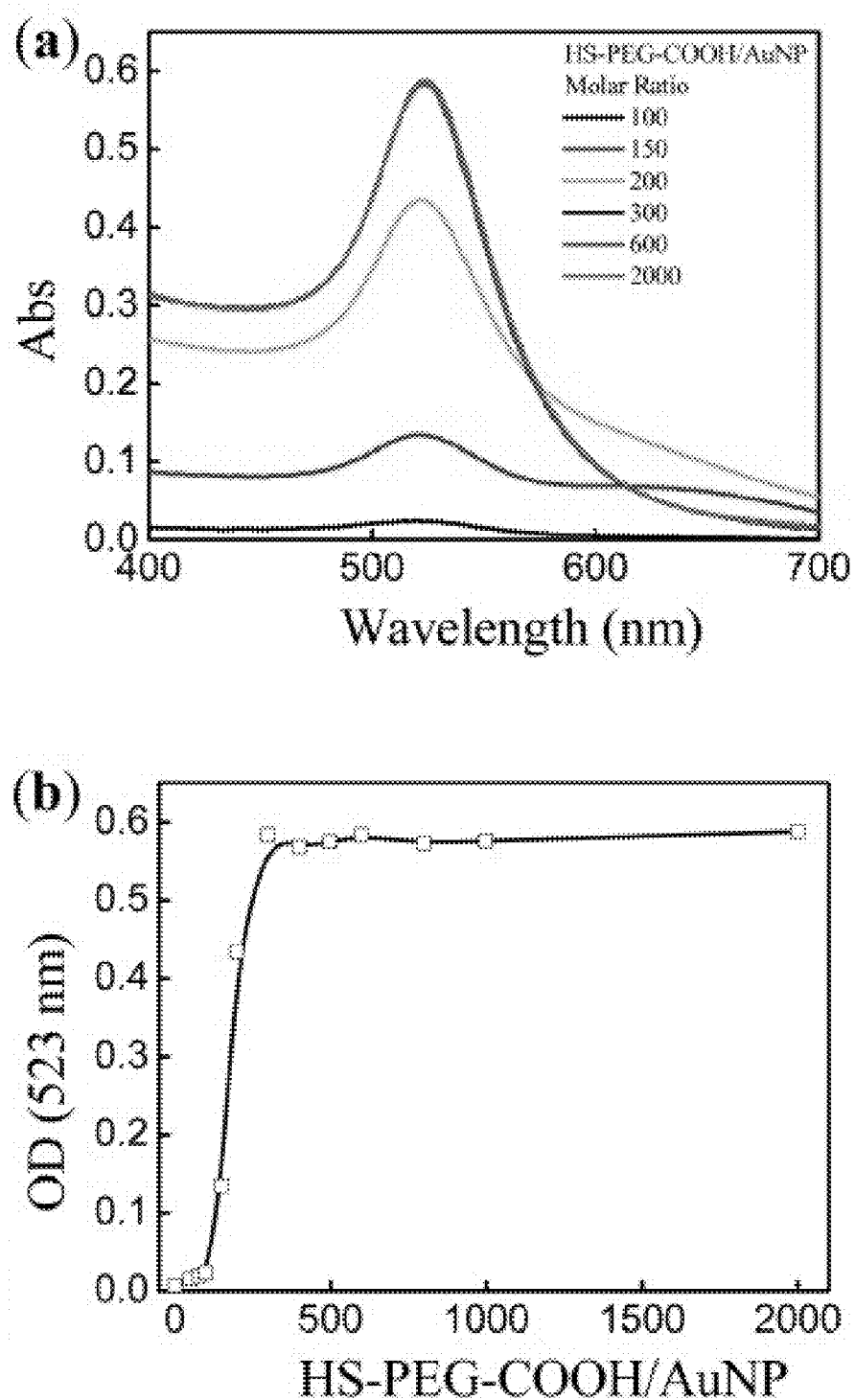
FIGS. 3a-b. (a) Absorption spectra at typical molar ratios and (b) optical density at absorption peak of gold nanoparticles PEGylated with HS-PEG-COOH at each molar ratio after centrifugation.

The differential PEG-COOH chain density on AuNPs after PEGylation at varying molar ratios of HS-PEG-COOH/AuNP was detected by centrifuging the solutions and re-suspending the pellet of AuNPs. For molar ratios less than 100 the pellet could not be re-dispersed after centrifugation, as shown in FIG. 3a, revealing the PEG-COOH chain density is too low to maintain a stable formulation. As the molar ratio increases from 100 to 200 the absorption spectra show that more AuNPs are recovered after centrifugation, determined by the increase of the absorption peak at 524 nm. However, detection of a second, smaller peak (or 'bump') at ~650 nm suggests these partially PEGylated AuNPs tend to form aggregates after centrifugation, indicating a higher PEG-COOH chain density is required to maintain stability. FIG. 3b shows the OD at the absorption peak of AuNPs PEGylated with HS-PEG-COOH at different molar ratios. The data clearly show which PEGylated AuNP formulations are stable after centrifugation, based on the PEG density on the AuNP surfaces. As the molar ratio increases from 100 to 300 the OD number increases by 25 times, with a relative change from 4% to 100% when compared to the OD before centrifugation, respectively. The data also indicate that even though the AuNP surfaces are not fully covered with PEG at a molar ratio of 300, the AuNPs are stable against centrifugation.

Figure 4:
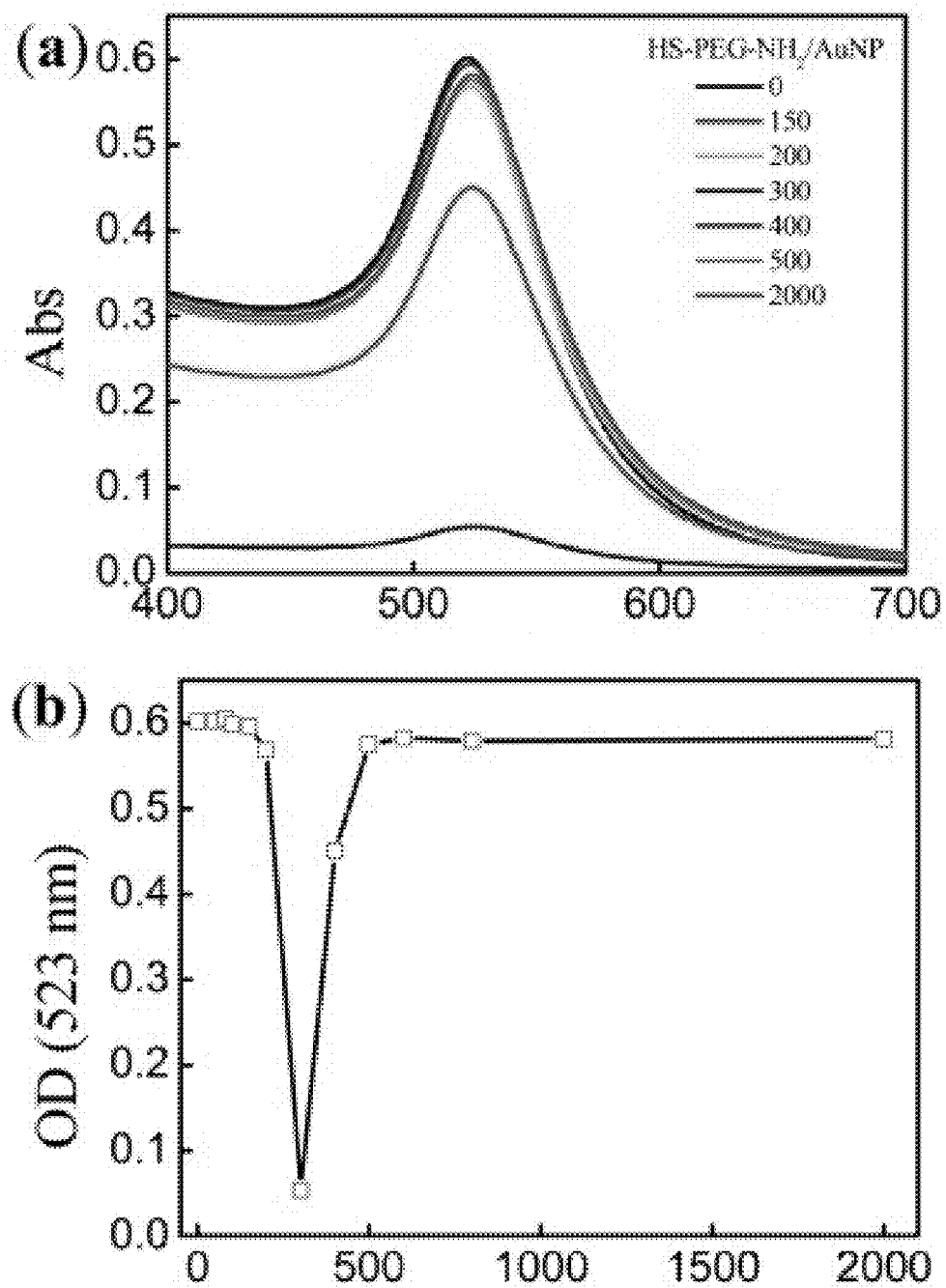
FIGS. 4a-d. (a) Absorption spectra at typical molar ratios, (b) optical density at absorption peak, (c) zeta potential, and (d) hydrodynamic size change of gold nanoparticles PEGylated with HS-PEG-NH$_2$ at each molar ratio before centrifugation.
Figure 4:
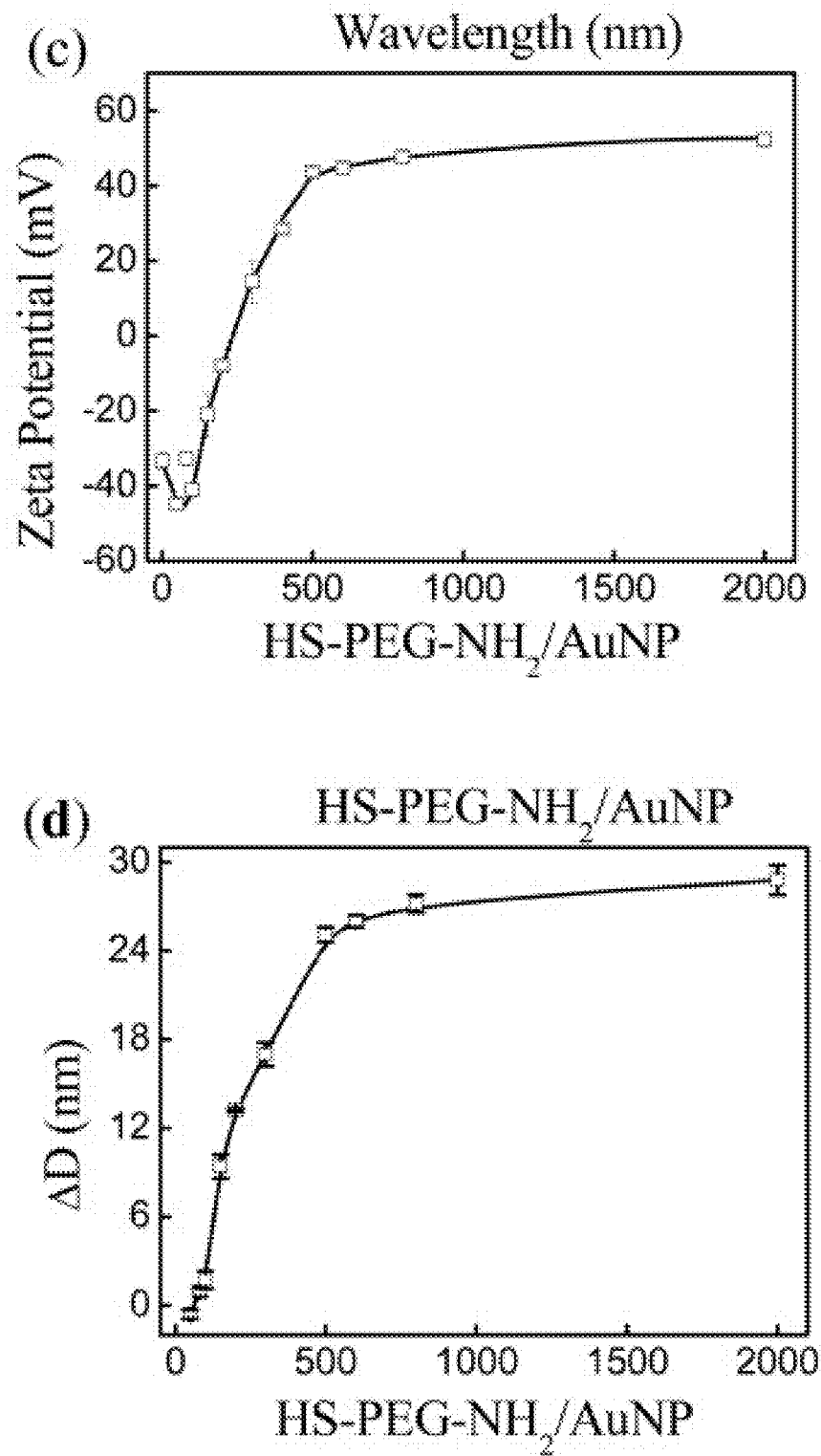

Furthermore, surface modification was carried out on gold nanoparticles with $HS-PEG-NH_2$ (thiolated positive charged PEG molecule terminated with amine group at its distal end). FIG. 4 shows the physical characteristics of AuNPs (~20 nm in diameter based on TEM imaging) after mixing with $HS-PEG-NH_2$ with different HS-PEG-COOH/AuNP molar ratios from zero to 2000. The AuNP concentration decreases after incubation at a range of molar ratios from 200 to 500. For the molar ratio of 300, a dip was observed in the OD for the peak wavelength of the absorption spectra after incubation with AuNPs as shown in FIGS. 4a and 4b. It is worth noting that the color of the solutions at these ratios does not change to purple and there are no bumps on any of the absorption spectra including that for a molar ratio of 300, revealing that the loss of the AuNPs was not because of aggregation of AuNPs. It was found that, at these molar ratio ranges, AuNPs become stuck on the Eppendorf tube (observing that the inside of the tube is red).

As the molar ratio of $HS-PEG-NH_2/AuNP$ increases from 50 to 300, the zeta potential of PEGylated AuNPs transforms from highly negative (−44.9 mV) to slightly positive (+14.4 mV) as shown in FIG. 4c. As previously mentioned, at a molar ratio of 300 the AuNPs are only 60% fully covered. This data suggests that two factors attribute to the dip formation observed in FIG. 4b: a zeta potential close to zero and partial PEGylation. As discussed below, this unstable range can be avoided by addition of PEG molecules with opposite charges (e.g., HS-PEG-COOH) prior to adding, for example, $HS-PEG-NH_2$. As the molar ratio of $HS-PEG-NH_2/AuNP$ further increases to 500 the zeta potential reaches +52.2 mV and becomes constant when the molar ratio is higher than 500, indicating successful PEGylation with increasing $PEG-NH_2$ chain density on the AuNPs until the surfaces become saturated. Successful PEGylation was also demonstrated by monitoring the size increase after PEGylation with increasing HS-PEG-NH$_2$/AuNP molar ratios, as shown in FIG. 4*d*. The data show that the hydrodynamic layer thickness increases by 26 nm at the saturated HS-PEG-NH$_2$/AuNP molar ratio of 500, which is consistent with the PEGylation using HS-PEG-COOH. The data combined clearly reveal a controlled increase in the PEG-NH$_2$ chain density as one increases the HS-PEG-NH$_2$/AuNP molar ratio. Using conjugation of gold nanoparticles with HS-PEG-NH$_2$ molecules as an example, worked conducted during the development of embodiments of the present invention further analyzed the efficiency of PEGylation using a fluorescamine-based assay to quantify the concentration of free HS-PEG-NH$_2$ in the supernatant. In this assay a non-fluorescent fluorescamine reacts with a primary amine to generate a compound that emits fluorescence at 480 nm when excited at 390 nm. Originally developed for quantification of primary amines in biomolecules, this assay has sensitivity on the pM scale. In doing this experiment, the HS-PEG-NH$_2$ concentration was varied during incubation from 50 to 2000 nM while keeping the AuNP concentration constant at 1.0 nM. Therefore, the initial input molar ratio between HS-PEG-NH$_2$ and gold nanoparticle ranges from 50 to 2000.

Figure 5:
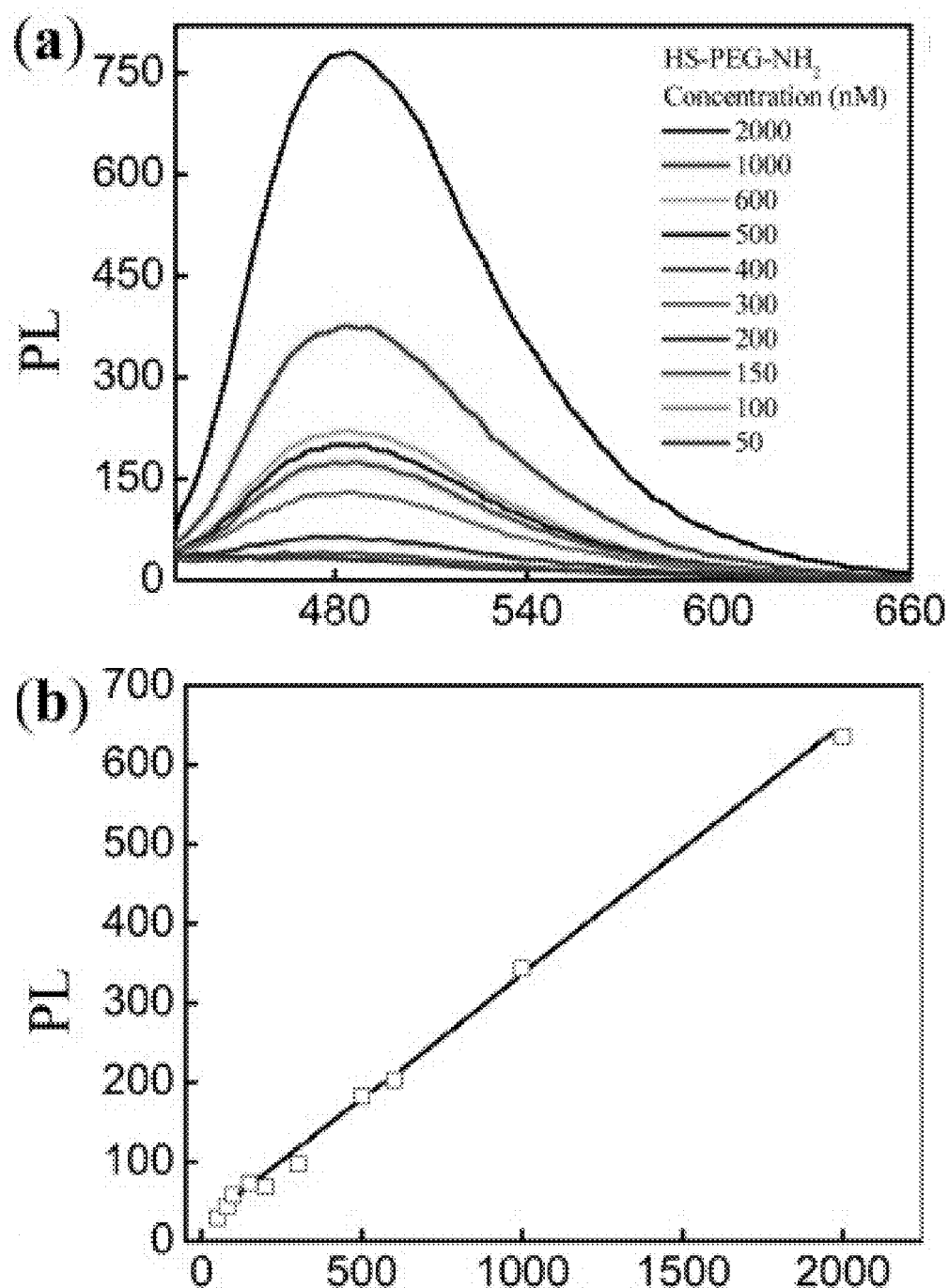
FIGS. 5a-d. Fluorescence spectra of the calibrating solutions (a) and the supernatants containing free HS-PEG-NH$_2$ after mixing with gold nanoparticles at different molar ratios followed by centrifugation (c). Corresponding fluorescence intensity at 480 nm versus HS-PEG-NH$_2$/AuNP molar ratios, prior to (b) and after (d) mixing with gold nanoparticles.
Figure 5:
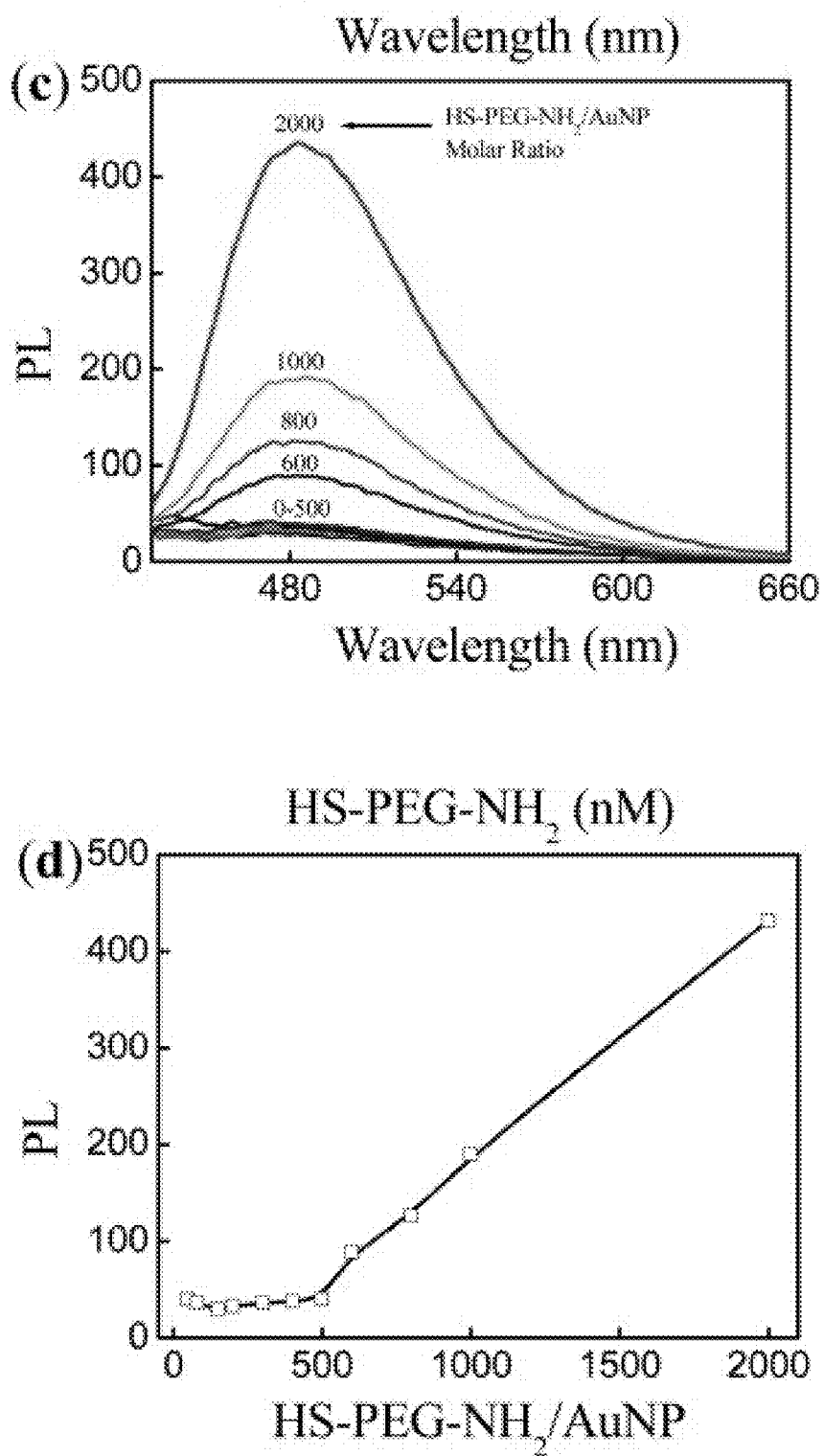

FIGS. 5*a* and 5*b* show the fluorescence spectra and the corresponding calibration curve that correlates the fluorescence intensity at 480 nm to the concentration of free HS-PEG-NH$_2$ without mixing with AuNPs. A linear relationship was found in the concentration range of 50 to 2000 nM of HS-PEG-NH$_2$. This assay was then applied to measure the free HS-PEG-NH$_2$ in the supernatants after incubation with AuNP at different molar ratios followed by centrifugation, shown in FIGS. 5*c* and 5*d*. Although the HS-PEG-NH$_2$ concentration increases 10 times up to 500 nM, there is no obvious fluorescence increase after measuring the supernatants until the PEGylation becomes saturated (at molar ratio of 500). This reveals that most of the added HS-PEG-NH$_2$ bind to AuNPs without any detectable free HS-PEG-NH$_2$ in the supernatants. Measuring the PEG concentration in supernatants to estimate the PEG chain density on AuNPs is a widely used method. When the ratio is higher than 500 one begins to see the fluorescence increase in the supernatant, indicating that the AuNPs gradually become saturated. This result is consistent with the zeta potential measurements. These combined experiments demonstrate a highly efficient PEGylation process that allows control of the PEG density on AuNPs by manipulating the molar ratio between HS-PEG-COOH or HS-PEG-NH$_2$ and AuNP, as long as the ratio is less than the saturated one.

Based on controllable stable conjugation of HS-PEG-COOH molecules and HS-PEG-NH$_2$ molecules on surface of gold nanoparticles described above with the surface coverage amount of HS-PEG-COOH molecules and HS-PEG-NH$_2$ molecules on the surface of the gold nanoparticles can be tuned to be any percent value between 0 and 100%. As such, the present invention allows methods of fabricating gold nanoparticles with zwitterionic surface, which permits precisely control of number of both negative charged ligands and positive charged ligands bound onto surface of gold nanoparticles. In certain embodiments, this method comprises: performing surface modification of gold nanoparticles for forming zwitterionic surface by conjugation of both negative charged ligands and positive charged ligands onto surface of colloidal gold nanoparticles in a sequential manner. Exemplary steps include the follows; Step 1: the negative charged ligands are first mixed with said colloidal suspension of gold nanoparticles at room temperature for at least 30 minutes. Step 2: addition of positive charged ligands to colloidal suspension of gold nanoparticles also at room temperature. The total amount of negative charged ligand added to the said colloidal gold nanoparticles is no more than the minimum amount required to provide a monolayer of bound negative charged ligand to the total of colloidal gold nanoparticles based on a footprint of negative charged ligand bound on gold nanoparticles and total amount of positive charged ligand added to the colloidal gold nanoparticles is no more than the minimum amount required to bind to all free binding sites left on surface of colloidal gold nanoparticles after conjugation of negative charged ligands onto surface of colloidal gold nanoparticles. Step 3: after mixing, the mixture is kept undisturbed for 24 hours at room temperature to provide a sufficient amount of time for both positive charged ligands and negative charged ligands to be conjugated onto the surfaces of colloidal Au nanoparticles; and optionally, after step 2 and before step 3, adding to colloidal gold nanoparticles more said negative charged ligands to ensure saturation of said binding sites on surface of said colloidal gold nanoparticles for maximizing colloidal stability of said colloidal gold nanoparticles.

Figure 6:
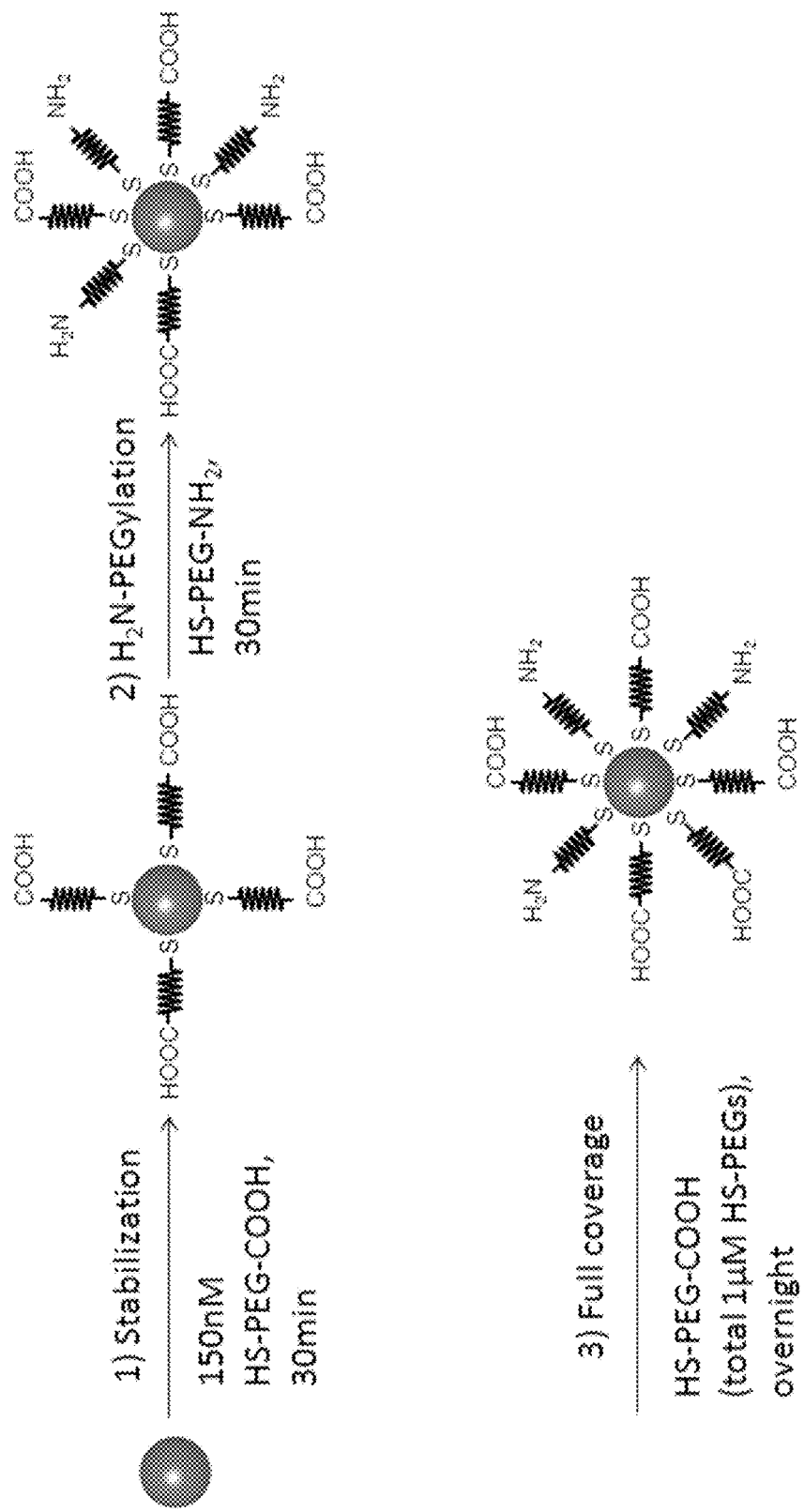
FIG. 6. Schematic illustration of fabrication of gold nanoparticles with zwitterionic surface bearing both PEG-COOH molecules and PEG-NH$_2$ molecules on their surface in a sequential manner.

As an example, work conducted during the development of embodiments of the present invention used the above method to fabricate gold nanoparticles with zwitterionic surface containing both HS-PEG-COOH molecules and HS-PEG-NH$_2$ molecules. The schematic illustration of fabrication of gold nanoparticles with zwitterionic surface bearing both PEG-COOH molecules and PEG-NH$_2$ molecules on their surface in a sequential manner is shown in FIG. 6. First partially PEGylating AuNPs with HS-PEG-COOH at room temperature for at least 30 minutes, then PEGylating with HS-PEG-NH$_2$. As long as the AuNPs are not saturated (e.g., the molar ratio between combined number of HS-PEG-COOH and HS-PEG-NH$_2$ and number of Au nanoparticles is lower than about 500), one can control the density of both HS-PEG-COOH and HS-PEG-NH$_2$ covalently attached to AuNPs. At least 30 minutes after addition of HS-PEG-NH$_2$, than adding more HS-PEG-COOH to saturate the surface for maximum AuNP stability. Finally, collection of fabricated gold nanoparticles with zwitterionic surface by centrifuge at 15000 g for 30 minute, removing the supernatant, and then redispersing into a phosphate buffered saline (PBS) with a PH of 7.4 prior to their use in cell experiments. In addition, power of fabricated gold nanoparticles with zwitterionic surface could be also formed after collection of them from solution.

Figure 7:
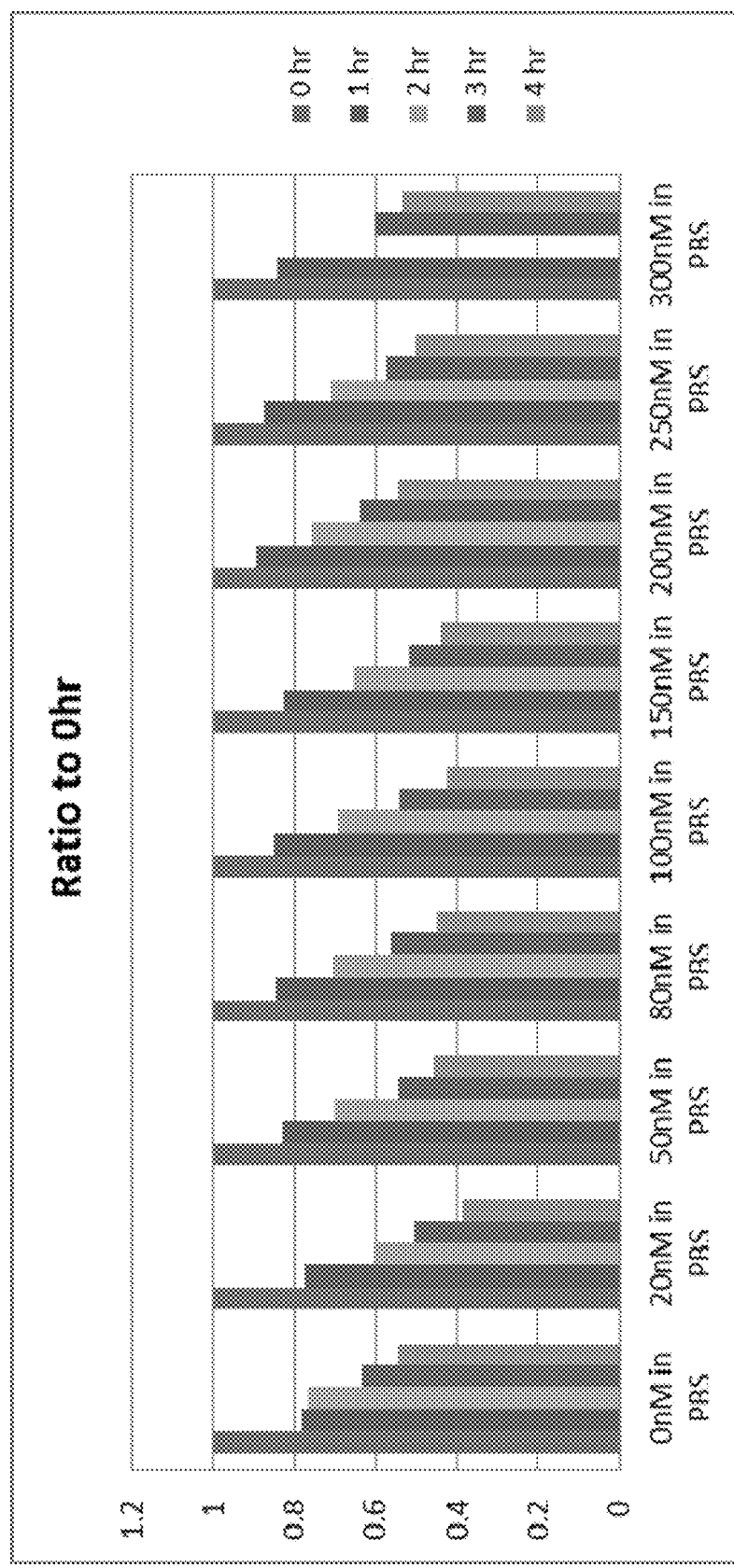
FIG. 7. Colloidal stability of gold nanoparticles bearing both PEG-COOH molecules and PEG-NH$_2$ molecules prepared in accordance with the present invention as function of time after dispersed in phosphate buffered saline (PBS), characterized by maximum absorbance of localized surface plasmon resonance of the gold nanoparticles around 520 nanometers, which is expressed as a percentage of that of control gold nanoparticles (absorbance at 0 hour). The number of PEG-COOH molecules bound onto surface of gold nanoparticle is fixed at 150 per gold nanoparticle and the number of PEG-NH$_2$ molecules bound onto surface of gold nanoparticle ranges from 0 to 300 per gold nanoparticle.

In work conducted during the development of embodiments of the present invention, a series of colloidal solutions of gold nanoparticles with zwitterionic surface have been made using method as shown in the FIG. 6. The molar ratio between the number of HS-PEG-COOH and the number of gold nanoparticles is fixed at 150 and the molar ratio between the number of HS-PEG-NH$_2$ and the number of gold nanoparticles ranges from 0 to 300. The stability of these obtained gold nanoparticles after redispersed into phosphate buffered saline (PBS) with a PH of 7.4 is examined and the results are shown in the FIG. 7. For all obtained gold nanoparticles, they are very stable. Two hours after being redispersed into PBS buffer, the decrease of surface plasmon resonance of gold nanoparticles is less than 40%. Thus, the method could fabricate gold nanoparticles having zwitterionic surface containing both HS-PEG-COOH and HS-PEG-NH$_2$ with their surface coverage could be controlled to be any amount between 0 and 100%, which are stable in phosphate buffered saline. The term "stable" means that the decrease of absorbance intensity caused by localized surface plasmon resonance of gold nanoparticles at 518 to 530 nm, more specifically at 520 nm two hours after redispersing gold nanoparticles into PBS buffer is less than 40% compared to the absorbance measured at time zero (immediately after resdispersing).

Figure 8:
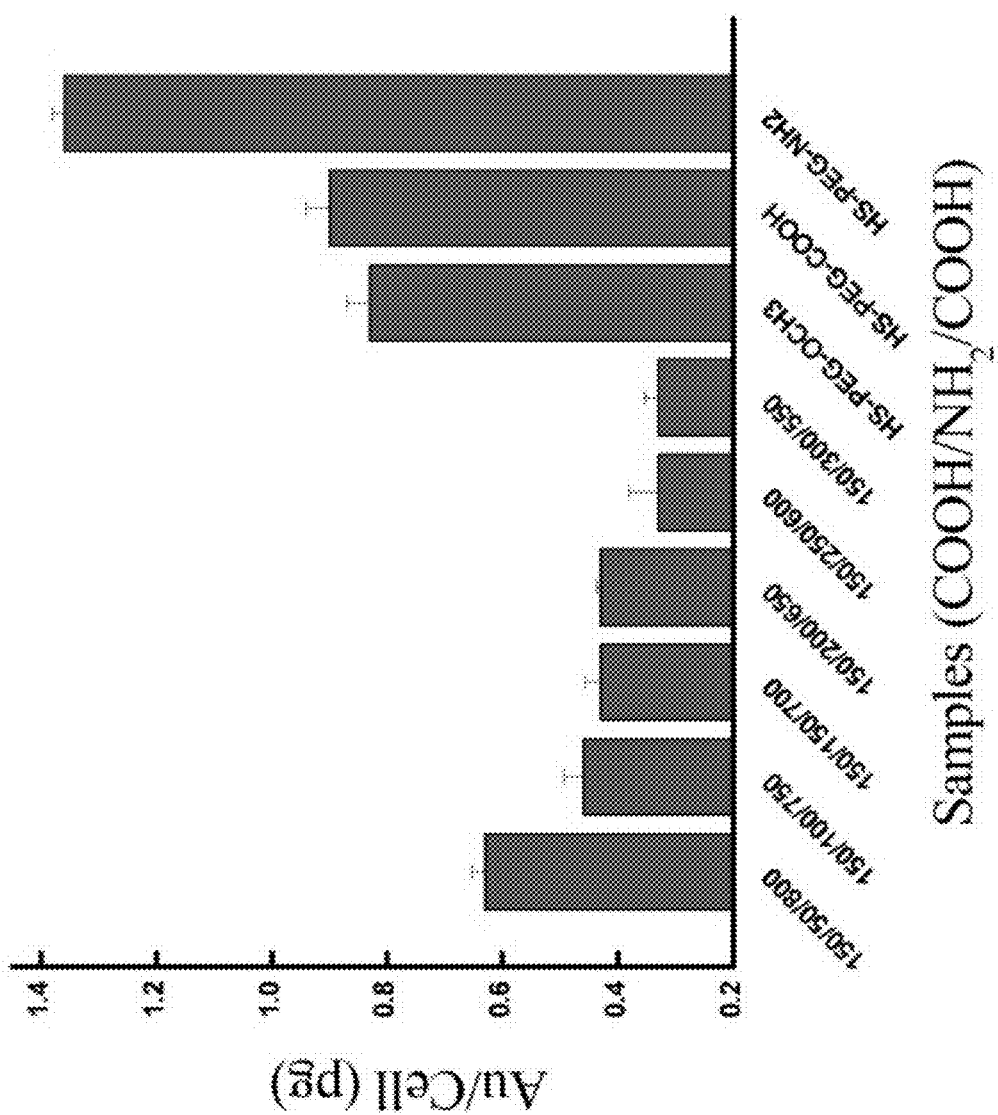
FIG. 8. Comparison of macrophage cells' non-specific uptake of gold nanoparticles having zwitterionic surface via conjugation of both HS-PEG-COOH molecules and HS-PEG-NH$_2$ molecules on the same gold nanoparticle with that of gold nanoparticles decorated with only HS-PEG-COOH, HS-PEG-NH$_2$, or HS-PEG-OCH$_3$.

Next, non-specific uptake of obtained gold nanoparticles was tested with zwitterionic surface by macrophage cells. As shown in FIG. 8, the data show that as the amount of PEG-$NH_2$ on AuNPs increases from 50 to 300, the non-specific uptake of Au/cell (pg) decreases by half from 0.63±0.01 to 0.33±0.01. The reduced cell uptake is likely due to the overall surface charge becoming more neutral with addition of more PEG-$NH_2$. As shown in the table 1, with fixed amount of PEG-COOH, the increase of amount of PEG-$NH_2$ do increase the zeta potential of gold nanoparticle from −48 mV, −35 mV, −17 mV, and to −2 mV as increasing amount of PEG-$NH_2$ per gold nanoparticle from 0 to 500.

TABLE 1

| Sample Name | Zeta Potential (mV) |
| --- | --- |
| COOH/NH2_150/0 | −48.2 |
| COOH/NH2_150/100 | −34.9 |
| COOH/NH2_150/300 | −17.1 |
| COOH/NH2_150/500 | −2.4 |
| COOH/NH2_150/700 | 13.6 |
| COOH/NH2_150/900 | 24.3 |

Table 1 shows the Zeta potential of gold nanoparticles with zwitterionic surface as function of number of PEG-COOH molecules and PEG-$NH_2$ molecules bound onto surface of gold nanoparticles. The number of PEG-COOH per gold nanoparticle is fixed at 150 and the number of PEG-$NH_2$ ranges from 0 to 900.

Furthermore, these AuNPs with zwitterionic surface have significant less non-specific uptake than the control AuNPs decorated with a single type of PEG-R (i.e. —$OCH_3$, —COOH, —$NH_2$). For instance, the double-charged AuNPs show a relative uptake ranging from 40% to 76% when compared to AuNP-PEG-$OCH_3$, the control with the least uptake.

Various chemical functional groups, such as thiol, amine, disulfide, and phosphine, possess a high affinity for the surface of gold nanoparticles. Thiol groups are considered to show the highest affinity for gold surfaces, approximately 200 kJ/mol, and therefore a majority of gold nanoparticle surface functionalization occurs through using ligand molecules having thiol groups which bind to surfaces of gold nanoparticles via a thiol-Au bond.

In addition to PEG or poly(ethylene oxide) (PEO) polymer, other polymers having molecular weight in the range of from 200 Daltons to 100,000,000 Daltons selected from but not limited to poly(2-(methacryloyloxy)ethyl phosphorylcholine), poly(2-(dimethylamino)ethyl methacrylate), poly(acrylic acid), and poly(ethylene glycol) containing at least one functional group having an affinity for surface of said gold nanoparticles could also be used as functional ligand.

In certain embodiments, the Au nanoparticles have the shape of a sphere, rod, prism, disk, cube, or core-shell structures, cages, and frames, wherein they have at least one dimension in the range of from 1 to 200 nm (e.g., 1 . . . 50 . . . 100 . . . 150 . . . or 200 nm). In addition, the method of surface modification described in this invention can be used for structures (e.g., nano structures) which have outer surfaces that are only partially covered with gold.

Thus, while only certain embodiments have been specifically described herein, it will be apparent that numerous modifications may be made thereto without departing from the spirit and scope of the invention. Further, acronyms are used merely to enhance the readability of the specification and claims. It should be noted that these acronyms are not intended to lessen the generality of the terms used and they should not be construed to restrict the scope of the claims to the embodiments described therein.

It is intended that the invention not be limited by the specific embodiments and their variations and combinations as described herein-above.

We claim:

1. A method for making conjugated gold nanoparticles comprising:
 a) providing:
  i) naked gold nanoparticles, wherein each of said naked gold nanoparticles has an gold surface, and wherein at least 90% of said gold surface is exposed and not attached to any molecules, and
  ii) first type of attachment molecules having the formula R1-polymer-R2, wherein R1 is a moiety having affinity for said gold surface of said naked gold nanoparticles, and wherein R2 is a functional group that allows attachment to other chemicals, and/or comprises a targeting ligand, and
  iii) second type of attachment molecules having the formula R3-polymer-R4, wherein R3 is a moiety having affinity for said gold surface, and wherein R4 is a functional group that allows attachment to other chemicals, and/or comprises a targeting ligand, and
 wherein either: A) said first type of attachment molecules possess a positive charge and said second type of attachment molecules possess a negative charge, or B) said first type of attachment molecules posses a negative charge and said second type of attachment molecules posses a positive charge;
 b) mixing said first type of attachment molecules with said naked gold nanoparticles in a first molar ratio of said first type of attachment molecules to said naked gold nanoparticles such that said first type of attachment molecules attach to said naked gold nanoparticles at a density level below the saturation level for said naked gold nanoparticles thereby generating unsaturated conjugated gold nanoparticles; and
 c) mixing said second type of attachment molecules with said unsaturated conjugated gold nanoparticles in a second molar ratio of said second type of attachment molecules to said unsaturated conjugated gold particles such that said second type of attachment molecules attach to said unsaturated conjugated gold nanoparticles thereby generating double-conjugated gold nanoparticles, and
 wherein said double-conjugated gold nanoparticles posses a ratio of negative to positive attachment molecules of 900/100 to 700/300.

2. The method of claim 1, further comprising providing a third type of attachment molecules having the formula R5-polymer-R6, wherein R5 is a moiety having affinity for said gold surface of said double-conjugated gold nanoparticles, and wherein R6 is a functional group that allows attachment to other chemicals, and/or comprises a targeting ligand, and step d) mixing said third type of attachment molecules with said double-conjugated gold nanoparticles in a third molar ratio of said third type of attachment molecules to said double-conjugated gold particles such that said third type of attachment molecules attach to said double-conjugated gold nanoparticles thereby generated third-conjugated gold nanoparticles.

3. The method of claim 1, wherein said R1 is the same or different on each of said first type of attachment molecules and is selected from the group consisting of: a thiol group, an amine group, a phosphine group, and a disulfide group.

4. The method of claim 1, wherein said R3 is the same or different on each of said second type of attachment molecules and is selected from the group consisting of: a thiol group, an amine group, a phosphine group, and a disulfide group.

5. The method of claim 1, wherein said polymer in said first type of attachment molecules comprises polyethylene glycol.

6. The method of claim 1, wherein said polymer in said first type of attachment molecules is selected from the group consisting of: polyethyleneglycol (PEG), polyacrylamide, polydecylmethacrylate, polystyrene, dendrimer molecule, polycaprolactone (PCL), polylactic acid (PLA), poly(lactic-co-glycolic acid) (PLGA), polyglycolic acid (PGA), polyhydroxybutyrate (PHB), and the said polymer has degree of polymerization in the range from 1 unit to 100 units.

7. The method of claim 1, wherein said polymer in said second type of attachment molecules comprises polyethylene glycol.

8. The method of claim 1, wherein said polymer in said second type of attachment molecules is selected from the group consisting of: polyethyleneglycol (PEG), polyacrylamide, polydecylmethacrylate, polystyrene, dendrimer molecule, polycaprolactone (PCL), polylactic acid (PLA), poly(lactic-co-glycolic acid) (PLGA), polyglycolic acid (PGA), polyhydroxybutyrate (PHB), and the said polymer has degree of polymerization in the range from 1 unit to 100 units.

9. The method of claim 1, wherein said R2 is selected from the group consisting of COOH, —OCH3, and —NH2.

10. The method of claim 1, wherein said R4 is selected from the group consisting of COOH, —OCH3, and —NH2.

11. The method claim 1, wherein at least 93% of said gold surface of each of said naked gold nanoparticles is exposed and not attached to any molecules.

12. The method of claim 1, wherein said naked gold nanoparticles are in a colloidal suspension.

13. The method of claim 1, wherein said naked gold nanoparticles are pulse laser ablation generated naked gold nanoparticles.

* * * * *